United States Patent
Paul, Jr.

(10) Patent No.: US 10,639,061 B2
(45) Date of Patent: May 5, 2020

(54) DEVICES AND METHODS FOR MODIFYING VEINS AND OTHER BODILY VESSELS

(71) Applicant: Cook Medical Technologies LLC, Bloomington, IN (US)

(72) Inventor: Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 314 days.

(21) Appl. No.: 14/536,000

(22) Filed: Nov. 7, 2014

(65) Prior Publication Data

US 2015/0133978 A1    May 14, 2015

Related U.S. Application Data

(60) Provisional application No. 61/902,571, filed on Nov. 11, 2013.

(51) Int. Cl.
*A61B 17/3207* (2006.01)
*A61B 17/00* (2006.01)
*A61B 17/32* (2006.01)

(52) U.S. Cl.
CPC ........ *A61B 17/320725* (2013.01); *A61B 17/00008* (2013.01); *A61B 2017/320004* (2013.01); *A61B 2017/320741* (2013.01)

(58) Field of Classification Search
CPC ...... A61B 17/320725; A61B 17/00008; A61B 2017/320004; A61B 2017/320741
See application file for complete search history.

(56) References Cited

U.S. PATENT DOCUMENTS

| | | | | |
|---|---|---|---|---|
| 5,030,201 A | * | 7/1991 | Palestrant | A61B 17/320725 600/568 |
| 5,376,100 A | * | 12/1994 | Lefebvre | A61B 17/320725 604/22 |
| 5,611,357 A | | 3/1997 | Suval | |
| 5,611,358 A | | 3/1997 | Suval | |
| 6,712,812 B2 | * | 3/2004 | Roschak | A61B 8/12 606/41 |
| 6,796,989 B2 | * | 9/2004 | Uflacker | A61B 17/320725 606/159 |

(Continued)

FOREIGN PATENT DOCUMENTS

WO   WO 2004/112569 A2   12/2004

*Primary Examiner* — Phong Son H Dang
(74) *Attorney, Agent, or Firm* — Woodard, Emhardt, Henry, Reeves & Wagner, LLP

(57) ABSTRACT

The present disclosure provides, in certain aspects, unique products and methods for abrading or otherwise disrupting an interior surface of a bodily a vessel. In some forms, these products and methods further incorporate the use of one or more occluding members to be deployed in the bodily vessel in and/or around a disrupted vessel region. Abrasive endoluminal devices, in certain embodiments, exhibit a low-profile first condition for delivery into and/or through the vasculature. The device can then be transitioned to a second, expanded condition inside the vasculature for carrying out a desired abrasion. With these types of devices, the manner and design by which the device transitions from a first condition to a second condition can vary. Embodiments of such are disclosed herein.

9 Claims, 12 Drawing Sheets

(56) References Cited

U.S. PATENT DOCUMENTS

| | | | |
|---|---|---|---|
| 7,678,123 B2 * | 3/2010 | Chanduszko | A61B 17/0057 606/139 |
| 2002/0010418 A1 | 1/2002 | Lary et al. | |
| 2003/0120256 A1 | 6/2003 | Lary et al. | |

* cited by examiner

DEVICES AND METHODS FOR MODIFYING VEINS AND OTHER BODILY VESSELS

CROSS-REFERENCE TO RELATED APPLICATION

This application claims the benefit of U.S. Provisional Application No. 61/902,571 filed Nov. 11, 2013, which is hereby incorporated by reference.

BACKGROUND

The present disclosure relates generally to medical technology and in particular aspects to devices and methods for occluding vascular vessels.

As further background, there are a variety of reasons why it is desirable to occlude or otherwise modify fluid flow through vascular vessels and other openings and passageways in the body. A vessel might be occluded, for example, to treat an aneurysm, arteriovenous (AV) fistula, incompetent venous valve or other blood vessel complication. Vascular vessels are comprised of tissue and are conduits for circulating blood through a mammalian body. A vascular vessel that carries blood from the heart is known as an artery. A vascular vessel that returns blood to the heart is known as a vein. There are three types of veins in a human: deep veins, which are located deep in the body close to the bones; superficial veins, which are located close to the skin; and perforating veins, which are smaller veins that connect the deep veins to the superficial veins.

To assist blood flow, venous vascular vessels contain venous valves. Each venous valve is located inside the vein and typically includes at least two valve leaflets, which are disposed annularly along the inside wall of the vein. These leaflets open to permit blood flow toward the heart and close, upon a change in pressure such as a transition from systole to diastole, to restrict the back flow of blood. When blood flows towards the heart, the venous pressure forces the valve leaflets to move apart in a downstream flexing motion, thereby creating an open path for blood flow. The leaflets normally flex together when moving in the upstream direction; therefore, they return to a closed position to restrict or prevent blood flow in the upstream, or retrograde, direction after the venous pressure is relieved. The leaflets, when functioning properly, extend radially inward toward one another such that the leaflet tips, or cusps, contact each other when the valve is closed.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood will collect, or pool in vessels beneath the valve. This pooling of blood causes an increase in the venous pressure below the valve. Venous valves that allow such deleterious retrograde flow are known as incompetent or inadequate venous valves. The condition resulting from such incompetent venous valves is known as venous valve insufficiency.

In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

A common method of treatment for venous valve insufficiency is the placement of an elastic stocking around the patient's leg to apply external pressure to the vein, forcing the walls radially inward to force the leaflets into apposition. Although sometimes successful, the tight stocking is quite uncomfortable, especially in warm weather, because the stocking must be constantly worn to keep the leaflets in apposition. The elastic stocking also affects the patient's physical appearance, thereby potentially having an adverse psychological affect. This physical and/or psychological discomfort can lead to the patient removing the stocking, thereby inhibiting treatment.

Surgical methods for treatment of venous valve insufficiency have also been developed. A vein with incompetent venous valves can be surgically constricted to bring incompetent leaflets into closer proximity in hopes of restoring natural valve function. Methods for surgical constriction of an incompetent vein include implanting a frame around the outside of the vessel, placing a constricting suture around the vessel (e.g., valvuloplasty), or other types of treatment to the outside of the vessel to induce vessel contraction. Other surgical venous valve insufficiency treatment methods include bypassing or replacing damaged venous valves with autologous sections of veins containing competent valves.

Another surgical method includes vein stripping and ligation. In this procedure, the femoral vein and other major venous tributaries are disconnected from the greater saphenous vein (GSV) and tied off. Next, the GSV is removed from the leg by advancing a wire through the vein, tying the wire to a saphenous vein end, and then pulling the wire, and vein, out through an incision in the upper calf or ankle. Unfortunately, the above surgeries require at least one incision and have several undesirable side effects and risks, such as a long patient recovery time, the potential for scarring, and numerous other risks inherent with surgery, such as those associated with the administration of anesthesia.

Various implantable prosthetic devices and minimally invasive methods for implantation of these devices have been suggested to treat venous valve insufficiency. Such prosthetic devices can be inserted intravascularly, for example from a catheter. Prosthetic devices can function as a replacement venous valve, or enhance venous valve function by bringing incompetent valve leaflets into closer proximity. In one procedure, venous valve function can be enhanced by clipping the valve leaflets together with a clip made from a biocompatible material, such as a metal or polymer.

Recently, a number of methods have been suggested to treat varicose veins and venous valve leaflets with energy sources, such as radiofrequency (RF) energy. In one such method, valve leaflets can be fastened together with electrodes delivering RF energy. In another such method, a catheter having an electrode tip can be used to apply RF energy to cause localized heating and corresponding shrinkage of venous tissue. After treatment of one venous section is complete, the catheter can be repositioned to treat a different venous section. Other known disruption techniques involve the use of laser energy such as with endovenous laser therapy (EVLT).

Methods for treatment of varicose veins have also been developed involving various forms of sclerotherapy. Generally, sclerotherapy involves the delivery of one or more sclerosing agents to the lumen of a varicose or other small diameter vein, which induces the vein to collapse and the venous walls to fuse, thereby closing the vein.

There remain needs for improved and/or alternative techniques, devices and systems for modifying vascular vessels. The present disclosure is addressed to those needs.

SUMMARY

The present disclosure provides, in certain aspects, unique products and methods for abrading or otherwise disrupting an interior surface of a bodily a vessel. In some forms, these products and methods further incorporate the use of one or more occluding members to be deployed in the bodily vessel in and/or around a disrupted vessel region. In this regard, one aspect of the present disclosure provides a medical product that can be used to abrade an interior surface of a vascular vessel, e.g., a venous vessel. In some instances, the present disclosure provides a catheter or other endoluminally advanceable device that has a linearly compressible segment occurring along a distal region of the device. The linearly compressible segment has a first end and a second end and an intermediate region that occurs between the first end and the second end. The intermediate region comprises an outwardly displaceable portion that is configured to move outwardly (e.g., radial expansion) toward an interior surface of the vascular vessel when the compressible segment is linearly compressed in the vessel. The outwardly displaceable portion comprises one or more abrasive adaptations for abrading the interior surface of the vessel. This product also comprises an actuating member that is actuatable (e.g., by translation along the endoluminally advanceable device) to linearly compress the compressible segment in the vessel.

A second aspect of the present disclosure provides a medical product that can be used to abrade an interior surface of a vascular vessel. This medical product has an endoluminally advanceable device that comprises a linearly compressible segment positioned along a distal region of the device. The compressible segment comprises an outwardly displaceable portion that is configured to move outwardly (e.g., radial expansion) toward an interior surface of the vascular vessel when the compressible segment is linearly compressed in the vessel. The outwardly displaceable portion comprises one or more abrasive adaptations for abrading an interior surface of the vascular vessel. The compressible segment is configured such that it is configurable between a first condition arranged for delivery through the vasculature and a second condition arranged for abrading an interior surface of a vascular vessel. The second condition comprises the compressible segment linearly compressed and the outwardly displaceable portion outwardly displaced relative to their respective positions in the first condition. In some forms, the compressible segment can be secured (e.g., locked) in the first condition and/or the second condition. This product further comprises an actuating member that is actuatable (e.g., translatable along the device) so as to transition the compressible segment from the first condition to the second condition. Optionally, an occluding member can be positioned in an interior region of the endoluminally advanceable device for deployment into the vessel.

Another aspect of the present disclosure provides a method for abrading an interior surface of a vascular vessel. In this method, a medical product that is the same or similar to that described above is provided, and the distal region of the device is located in a vascular vessel with the compressible segment in the first condition. The actuating member is then actuated to transition the compressible segment from the first condition to the second condition. Thereafter, the compressible segment while in the second condition is moved (e.g., by translation and/or rotation) through the vascular vessel from a first vessel location to a second vessel location so as to abrade an interior surface of the vessel.

A further aspect of the present disclosure provides a method for occluding a vascular vessel. In this method, a medical product that comprises an abrading member and an occluding member is delivered to a vascular vessel. The abrading member is such that it configurable between a first condition arranged for delivery through the vasculature and a second condition arranged for abrading an interior surface of a vascular vessel. Thereafter, the abrading member while in the second condition is moved (e.g., by translation and/or rotation) through the vascular vessel so as to abrade an interior surface of the vessel between a first vessel location and a second vessel location. The abrading member is then removed from the vascular vessel with the occluding member remaining in the vessel. The occluding member is left in the vessel such that it comprises a portion residing between the first vessel location and the second vessel location and in contact with an abraded interior surface of the vessel.

Another embodiment of the present disclosure provides a medical product for occluding a vascular vessel. This particular medical product is comprised of an endoluminally advanceable device that comprises an abrading member having an abrasive exterior surface. The endoluminally advanceable device further comprises an interior region communicating with a distal opening. The abrading member is such that it is configurable between a first condition arranged for delivery through the vasculature of a patient and a second condition arranged for abrading an interior surface of a vascular vessel. The second condition comprises the abrasive exterior surface outwardly displaced relative to its position in the first condition of the member. This product further comprises an occluding member that is removably positioned in the interior region of the device, and is deployable therefrom through the distal opening.

Yet another embodiment of the present disclosure is a method for occluding a vascular vessel that utilizes a product that is the same or similar to that described above. In this method, the endoluminally advanceable device is delivered to a vascular vessel with the abrading member in the first condition. The abrading member while in the second condition is then moved (e.g., by translation and/or rotation) through the vascular vessel so as to abrade an interior surface of the vessel between a first vessel location and a second vessel location. Thereafter, the occluding member is deployed from the interior region of the device through the distal opening, and the device is removed from the vascular vessel. The method is carried out such that the occluding member remains in the vessel and comprises a portion residing between the first vessel location and the second vessel location and in contact with an abraded interior surface of the vessel.

Other objects, embodiments, forms, features, advantages, aspects, and benefits of the present disclosure shall become apparent from the detailed description and drawings included herein.

DETAILED DESCRIPTION

Figure 1:
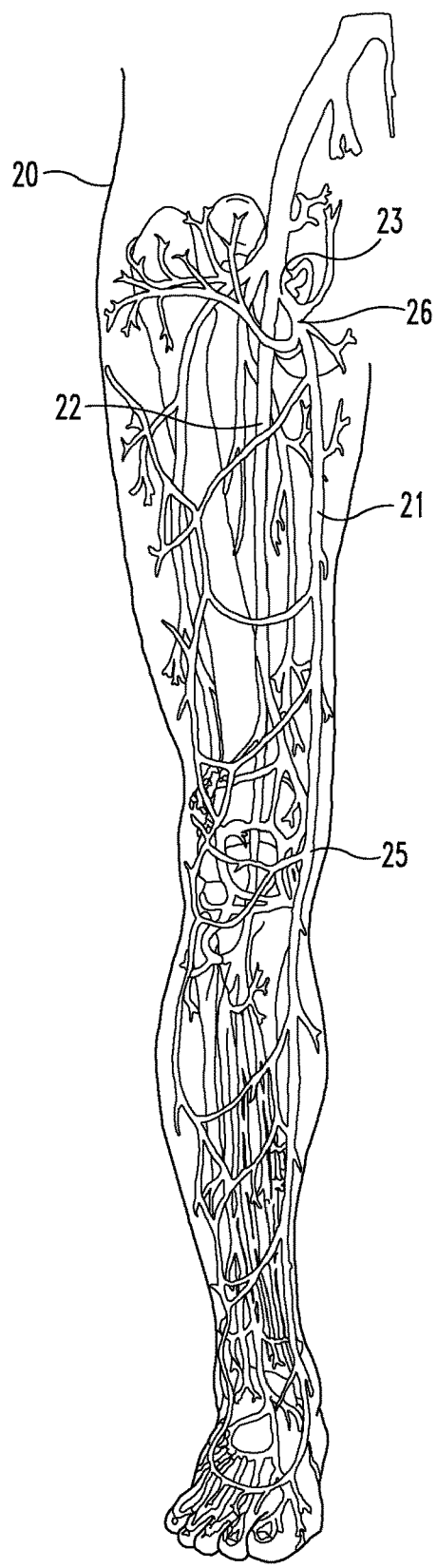
FIG. 1 depicts a human leg showing certain venous structures therein.

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the present disclosure is thereby intended. Any alterations and further modifications in the described embodiments and any further applications of the principles of the present disclosure as described herein are contemplated as would normally occur to one skilled in the art to which the disclosure relates.

As disclosed above, in certain aspects, the present disclosure provides unique products and methods for abrading or otherwise disrupting an interior surface of a bodily vessel. In some forms, useful devices can exhibit a low-profile first condition for delivery into and through the vasculature, e.g., in a non-abrading or substantially non-abrading fashion. The device can then be converted to a second condition inside the vasculature for carrying out a desired mechanical abrasion. This second condition, in some designs, will include a distal abrading component outwardly displaced (e.g., displaced radially outward) relative to its position in the first condition of the device. With this sort of product, the manner and design by which the abrading component moves outwardly can vary. In some forms, an abrading component will be constrained in a low-profile condition by a delivery sheath or other object positioned around the abrading component, and will expand when the constraining force is removed. Yet, abrading components can be differently constrained or altogether not constrained during delivery in other inventive embodiments. As well, inventive products and methods, in certain aspects, will involve the use of one or more occluding members to be deployed in the bodily vessel in and/or around a disrupted vessel region.

Inventive products and methods can be used to affect various passageways and openings in the body including those in the vasculature. With reference now more particularly to the figures, shown in FIG. 1 is a diagram of a human leg 20 showing certain venous structures therein. In particular, shown is human leg 20 having great saphenous vein (hereinafter "GSV") 21 and femoral vein 22 which adjoin at the sapheno-femoral junction 23. In accordance with certain aspects of the present disclosure, the GSV 21 can be treated in a region constituting any or all of the passage between a point 25 occurring near the medial side of the knee to a point 26 occurring prior to the sapheno-femoral junction 23. Desirably, such treatment will be effective to prevent reflux of venous blood from the sapheno-femoral junction 23 in a direction down toward the medial side of the knee (e.g., at point 25). Such occlusion is effective to treat varicosities that commonly occur in lower portions of the leg, e.g. portions occurring below the knee.

Figure 2:
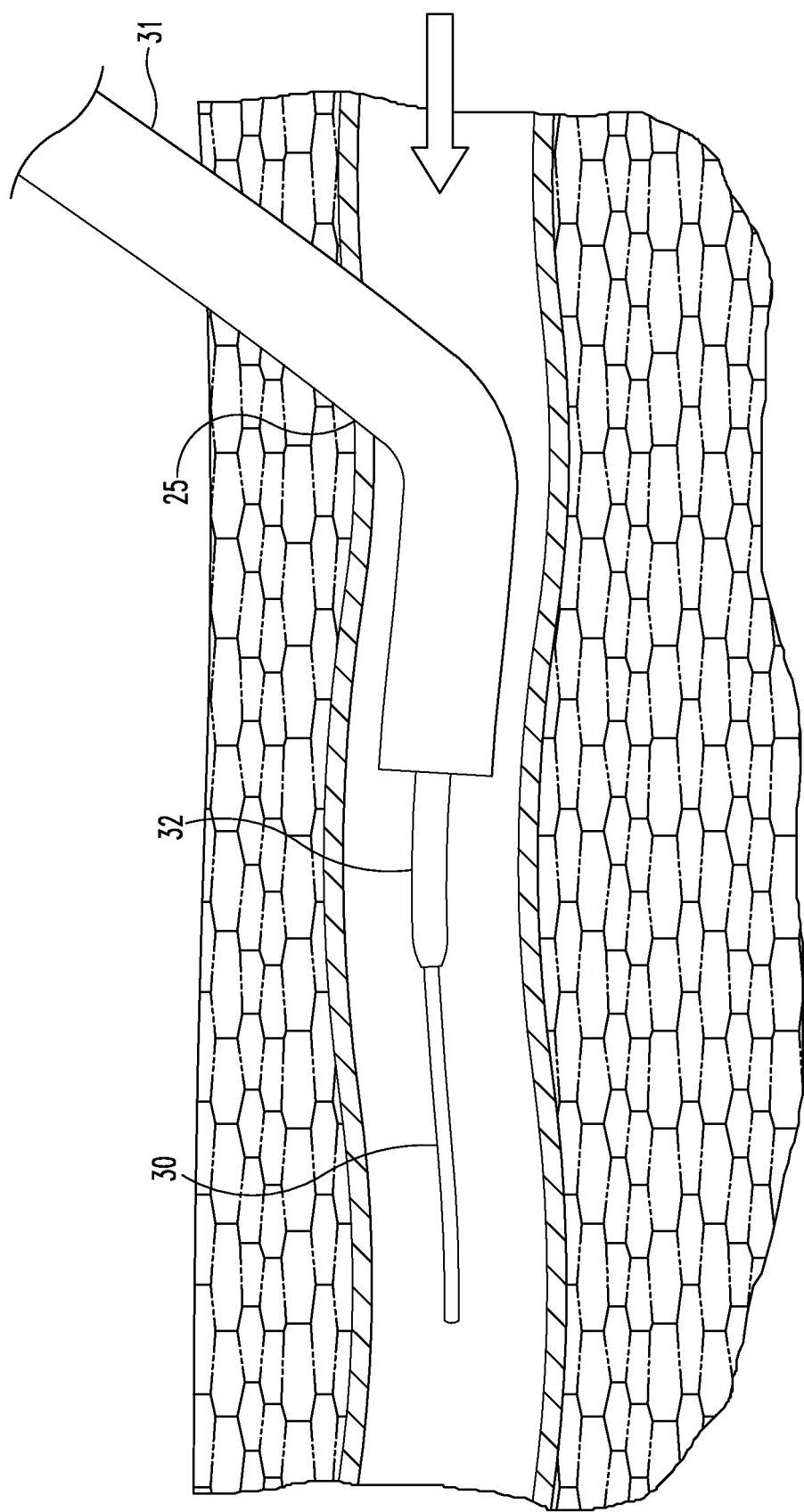
FIG. 2 depicts an illustrative deployment embodiment in a bodily vessel.

Turning more specifically now to FIG. 2, shown is an enlarged view of a bodily vessel. This vessel could, for example, represent a region of the GSV occurring generally between points 25 and 26 of FIG. 1. In an illustrative deployment procedure, percutaneous access to the GSV 21 can be achieved at point 25 using the Seldinger or any other suitable technique. For instance, an access needle (not shown) can be passed through the skin to access the GSV 21, and an elongate guiding member, such as a wire guide 30, can be passed through the access needle and into the vessel. In conjunction with or as part of an inventive method, wire guide 30 can be used for any number of conventional procedures including catheterization and imaging procedures to locate the sapheno-femoral junction 23 or other dilation procedures to open or otherwise straighten the GSV 21. After any such procedures are performed, the wire guide 30 can be removed or can be used to assist in the delivery of devices and materials within the GSV as described herein.

Specifically, referring still to the illustrative embodiment shown in FIG. 2, a deployment sheath 31 can be placed at a suitable location in the GSV 21 using a flexible guide catheter 32, or, alternatively, a suitable dilator or dilator tip mounted on the guide catheter. In placing or inserting the sheath 31 in the GSV, the guide catheter 32 can be first received over the wire guide 30 then pushed into the GSV 21 where it follows along the wire guide 30 to a location within the GSV 21. Next, the sheath 31 can be received over the guide catheter 32, pushed into the GSV 21, and follow the guide catheter 32 to a suitable location in the vessel. Alternatively, the sheath 31 and guide catheter 32 can be placed within the GSV 21, with the guide catheter 32 leading the sheath 31, and both can be pushed along the wire guide 30 until the sheath 31 is in a suitable location. Still alternatively, a steerable catheter can be used in conjunction with a sheath, thereby negating the need for a wire guide. Accordingly, inventive products and methods can utilize any number of sheaths, catheters, wires and/or other endoluminally advanceable devices, and these devices, alone or in combination, can be used to facilitate a vessel wall disruption. Illustrative sheaths such as sheath 31 can have an inner diameter (I.D.) ranging from about 4 French up to about 40 French. In accordance with certain aspects of the disclosure, the guide catheter 32 and wire guide 30 will be removed from the GSV 21, leaving sheath 31 in place with an empty lumen for receiving other devices and/or materials.

Figure 3A:
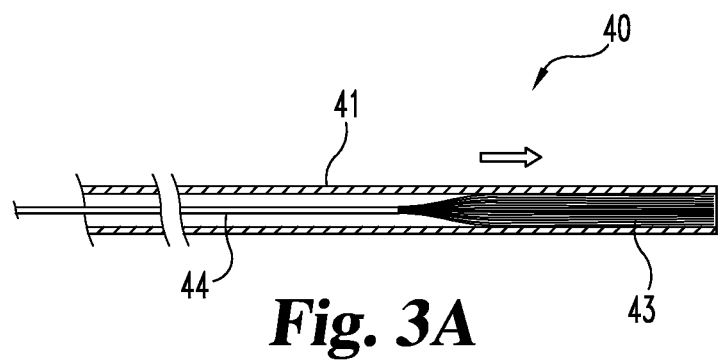
FIG. 3A is a partial view of an inventive medical product with an abrading member in a first condition.
Figure 3B:
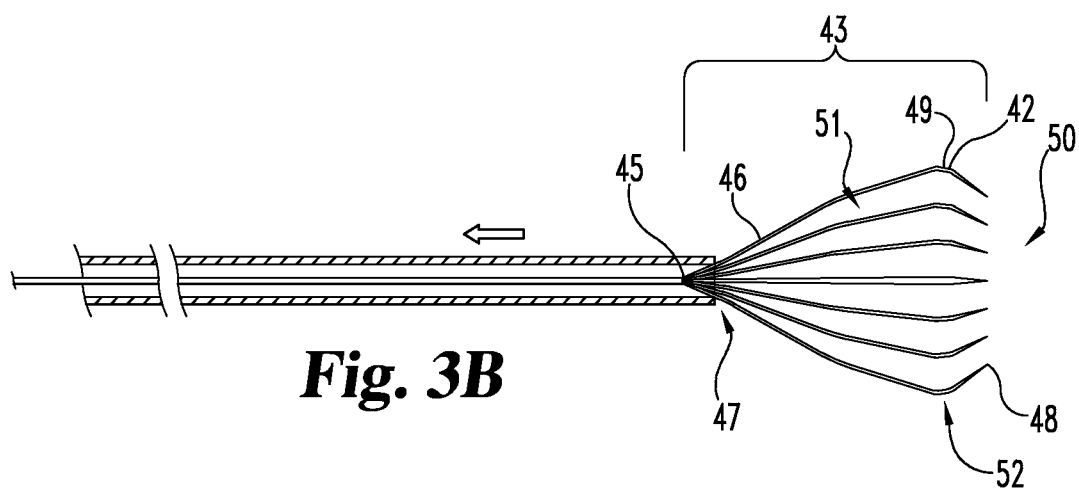
FIG. 3B shows the inventive product of FIG. 3A with the abrading member in a second condition.

FIG. 3A shows an inventive medical product 40 that can be delivered to a bodily vessel through emplaced sheath 31. Product 40 includes a flexible catheter 41 having a lumen. Product 40 also includes an abrading member 43 that extends distally from an actuating member, such as a wire or cable 44. This form of abrading member may be a separate component attached to the actuating member, or the two may be constructed as a single piece. FIG. 3A shows the abrading member constrained within the catheter lumen which, in turn, reduces the delivery profile of the member. Cable 44 is translatable through the catheter lumen, and in this regard, can be moved back and forth in the lumen to retract and deploy the abrading member as shown in FIGS. 3A and 3B, respectively.

In some instances, abrading member 43 includes one or more elongate arms 46 with a proximal end 45 positioned in a centralized region 47 and extending distally to a distal end 48 of the member. One or more or all arms 46 may be interconnected at the centralized region 47 and/or at other locations along the member. In many instances, the abrading member 43 is designed so that each of the arms 46 of a plurality of arms 46 will move outwardly in a generally radial fashion when the abrading member 43 is advanced from within flexible catheter 41 and is no longer constrained within the catheter lumen. Thus, when deployed, the distal ends 48 of arms 46 extend radially outward, so that arms 46 to form a conical or frusto-conical arrangement. In some instances, as illustrated in FIG. 3B, one or more arms 46 may include an optional bend 49 in a distal region of arm 46. The bend 49 can be designed to direct the tip of the arm away from the vessel wall when the device is deployed in a vessel, so that a side of the arms 46 and not the distal end 48 of the arm 46 contact the wall of the vessel. Alternatively, or additionally, bend 49 can be arranged so as to increase the amount of surface area of arm 46 contacting the wall of the vessel. While the abrading member 43 is intended to disrupt vessel tissue, bends and other similar adaptations can minimize the risk of having the abrading member pierce through and/or into the vessel wall in situations where such piercing would be undesirable. Further, in embodiments having this and similar arrangements, an opening 50 occurs at the distal end of the member which provides access to an interior region 51 of the member. An interior region 51 of this sort can provide space in which one or more occluding members and/or other devices or substances can reside as discussed elsewhere herein.

Figure 3C:
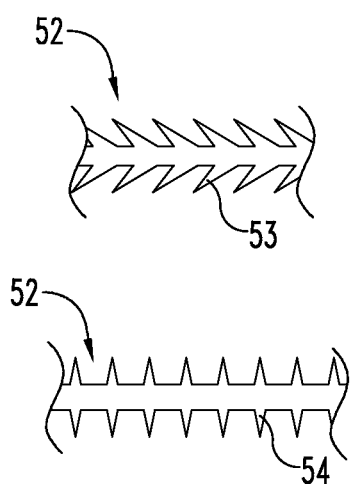
FIG. 3C illustrates a partial view of an abrading member.

A portion of abrading member 43, such as elongate arm 46, comprises one or more abrasive adaptations, such as an abrading surface 42 arranged to contact the inside surface of a bodily vessel, and, upon movement of the abrading surface 42 relative to the surface of the bodily vessel, abrade the surface of the bodily vessel. In some embodiments, abrading surface 42 is positioned on one or more or all of arms 46. For instance, an arm 46 can include a distal portion having a plurality of surface projections 52 arranged to abrade the inside wall of a bodily vessel. For instance, as illustrated in FIG. 3C, surface projections 52 may include blades 53, micro-points 54, or spines 56, or other projections as will be apparent to those of ordinary skill in the art. These types of arms 46 and other inventive components can be made abrasive in any suitable manner including by attaching silicon carbide particles or other suitable abrasive materials or devices to the component, by initially constructing the component to have sharp edges and/or projections (e.g., micro-spines, hooks, blades, etc.), by having objects project through an exterior surface of the component and/or in other suitable fashions as will be recognized by those skilled in the art. These types of surface constructions, modifications, etc. can enable a device to roughen, condition, de-epithelialize, or otherwise disrupt at least a portion of a vessel wall. The disruption of the vessel wall tissue can serve to initiate a localized healing response in patient tissue that can be advantageous in enhancing occlusion of the vessel. In some cases, such a disruption can cause or help cause an irreversible spasm and contraction of a vessel segment.

A variety of frame or frame-like devices can be adapted into abrading members in particular aspects of the disclosure. These various members can include single- and multiple-part frames. In some embodiments, an abrading member will include a filament or wire body or other similar frame or frame-like structure. Abrading members, in some aspects, can be designed to move between a first condition and one or more other conditions, for example, in the case of an abrading member that is compactable to a compacted, first condition, and when in this compacted condition, is then expandable to an expanded, second condition. In forms where an abrading member has the capacity to expand, these members can include those that are considered self-expanding and those that require at least some manipulation in order to expand.

Abrading members of this sort and other similar components useful in the present disclosure can be constructed using one or more pieces of superelastic wire or any of a variety of other suitable materials described herein or otherwise known to those skilled in the art including MRI compatible materials. Frames and other similar expandable and non-expandable devices, when utilized in the present disclosure, may be made from metallic or non-metallic material, or both. The non-metallic material can suitably be a synthetic polymeric material, including for example bioresorbable and/or non-bioresorbable plastics. Materials commonly used in medical device construction include biologically compatible metals, e.g., stainless steel, titanium, tantalum, gold, platinum, copper and the like, as well as alloys of these metals; synthetic polymeric materials; low shape memory plastic; a shape-memory plastic or alloy, such as Nickel Titanium (i.e., "Nitinol"); and the like.

In certain forms, a resilient abrading member will be provided in a relaxed condition. The member can then be deformed (e.g., collapsed, compressed, etc.) from this relaxed, first condition to a deformed, second condition and held there. In this deformed, second condition, the resilient member is then poised to essentially return to its relaxed, first condition. Illustratively, an abrading member can be compressed into a compressed condition (e.g., by folding one or more times and/or rolling portions of the member) for positioning in a delivery device lumen having a relatively smaller diameter than that which the member could otherwise fit in its relaxed condition. In this compressed condition, the member then has the ability to self-expand essentially back to its prior, relaxed condition upon being removed from the delivery device lumen. In other embodiments, frame-like abrading members exhibit little or no resiliency.

In some instances, an abrading member will be urged to expand by another device component exerting force on the abrading member. This can be made to occur with both self expanding and non-self expanding abrading members. Abrading members can be provided and delivered in a contracted state, and then expanded upon the application of a force to the member. Abrading members which take on a contracted state, but expand in response to a conditional change, e.g., a change in temperature such as may be incurred in a temperature transition from a first temperature below the body temperature of a patient, to the body temperature of the patient, can also be utilized. Abrading members having these or other characteristics may be used in embodiments of the present disclosure.

Figure 4:
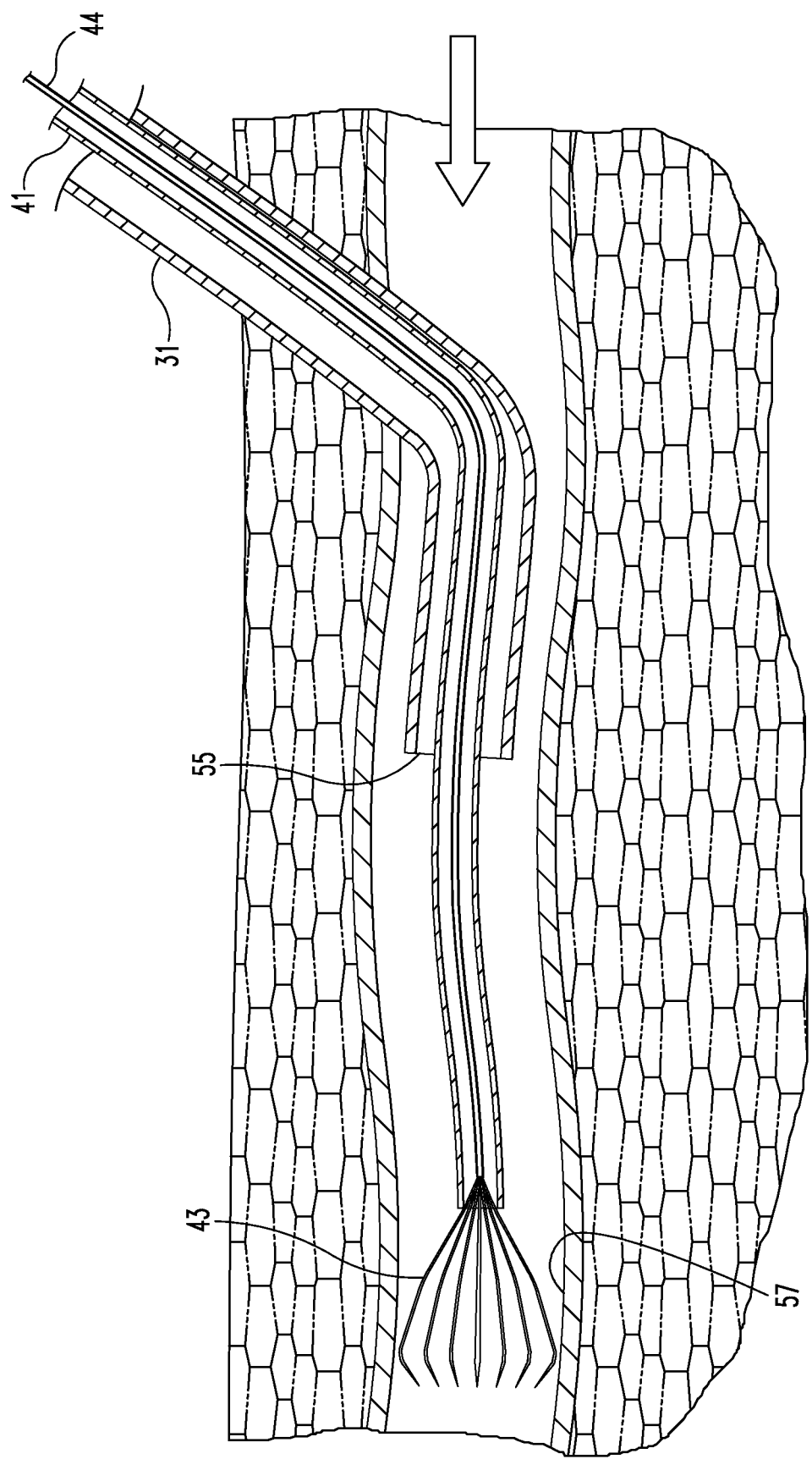
FIG. 4 shows an inventive medical product in a bodily vessel with an abrading member expanded within the vessel.

Continuing with the embodiment of FIGS. 3A and 3B, in an illustrative method, the abrading member can be retracted within the sheath, and this combination can be inserted into emplaced sheath 31 and advanced therethrough until it exits the sheath through its distal, open end 55. When desirably positioned in the vessel, abrading member 43 can be deployed from catheter 41 causing the plurality of arms 46 to move outwardly and contact an interior surface 57 of the vessel, as shown in FIG. 4. Deployment can be achieved by holding the sheath in place in the vessel and forcing the abrading member out of the sheath, by holding the abrading member steady and pulling back on the sheath, or a combination of the two. Upon deployment, the abrading member can then be moved back and forth in the vessel, rotated, vibrated and/or otherwise manipulated to cause a desirable abrasion of the vessel wall, whether done manually or with the assistance of a powered ancillary device. Thereafter, the abrading member can be removed from the body or relocated in the vessel to cause another abrasion. The outer sheath 31 can then also be removed from the body if no other treatments are to be performed. However, in some embodiments, sheath 31 will be left in place following an abrasion so that it can be used to carry out one or more additional steps such as delivering other implants, drugs, etc. as discussed herein. Alternative embodiments avoid the use of the catheter 41 by inserting abrading member 43 directly into sheath 31.

In certain aspects of the present disclosure, a post-abrasion step might include placing one or more occluding devices and/or other substances or materials (e.g., a drug, sclerosant, biotropic material, etc. as discussed herein) in the bodily vessel in and/or around an abraded region. In some inventive embodiments, one or more agents or other substances (see below) can be conjunctively or cooperatively emplaced within a patient during a vessel disruption step as discussed herein. Cooperative emplacement can include the contact of patient tissue with agents before, after, and/or while the disruption is being carried out, for example, by placing an agent on an abrading component, by passing an agent through an abrading component and/or in any other suitable manner as will be recognized by those skilled in the art. Such tissue contact of agents can occur in those areas that will become or are in contact with one or more occlusive devices and/or are adjacent to or near the implant or prospective implant location, when implants are employed. For example, the agents can be delivered into the patient through a cannulated lumen, such as before an occlusive device is implanted, or can be injected into a patient through a needle and syringe, such as after an occlusive device is implanted. In additional embodiments, the agents can be contained within or on an occlusive device, such as by being applied to an occlusive construct by a physician before implantation occurs, and/or by being doped, bonded, or otherwise contained within a dry occlusive construct, such as can be achieved by soaking a construct in one or more agents and thereafter drying and packaging the construct. In some instances, the abrading member 53 has an agent coating arranged to release (e.g., elute) an agent. For example, abrading surface 42 may comprise a drug coating.

A vessel surface can be contacted with any material (e.g., agent) conducive to achieving chronic occlusion of the vessel. In this regard, the delivered material may be a solid, liquid, gel, foam or gas, such as blood, polymer, contrast medium, a remodelable or bioabsorbable material, saline, a non-bioabsorbable material, collagen rods or particulates, a collagenous or gelatinous foam, air, chitosan, gelatin, oxidized regenerated cellulose, calcium alginate, alginate, thrombin-fibrin enhanced materials, fibrin glues, or any suitable combination thereof. In one embodiment, a comminuted, fluidized, and/or gelatinous remodelable material is delivered. For example, a remodelable gel can be formed from fluidized compositions, as illustrated in U.S. Pat. Nos. 5,275,826, 5,516,533, 6,206,931, and/or International Publication No. WO2005020847 (Cook Biotech Incorporated) published Mar. 10, 2005, which are each hereby incorporated by reference in their entirety.

In certain embodiments, a delivered material (e.g., agent) will include a substance that is capable of bringing about, inducing or furthering constriction, spasm, or closure in a bodily vessel of a patient and/or causing the de-epithelialization or inflammation (either dilative or constrictive), and/or otherwise initiating a healing response in patient tissue, such as a wall segment of a venous vessel. Such materials can include any suitable vasoconstrictive agent, sclerosive agent, thrombogenic agent, inflammatory agent, hypercoagulable agent, or any suitable combination of one or more of any of the above or other suitable agents. For example, suitable vasoconstrictive agents can include any suitable alpha adrenergic direct or indirect agonist, such as norepinephrine, epinephrine, phenylephrine, and/or cocaine, or lidocaine, hypertonic saline, or any suitable combination thereof. Illustrative sclerosive agents can include, for example, polidocanol, sodium tetradecyl sulfate, e.g. SOTRADECOL®, morrhuate sodium, ethanolamine oleate, tetradecyl sulfate, tetracycline, glycerin, hypertonic glucose, talc, acetic acid, alcohol, bleomycin, picibanil, ethibloc, deoxycycline, and/or any suitable microfoam that contains a sclerosive agent, such as VARISOLVE®, manufactured by Provensis, Ltd. of London, England, or any other suitable agent as disclosed in U.S. Pat. Nos. 5,676,962 and/or 6,572,873, for example. In some aspects, an anesthetic agent may be added to a sclerosant agent mixture or other deliverable material.

Figure 5:
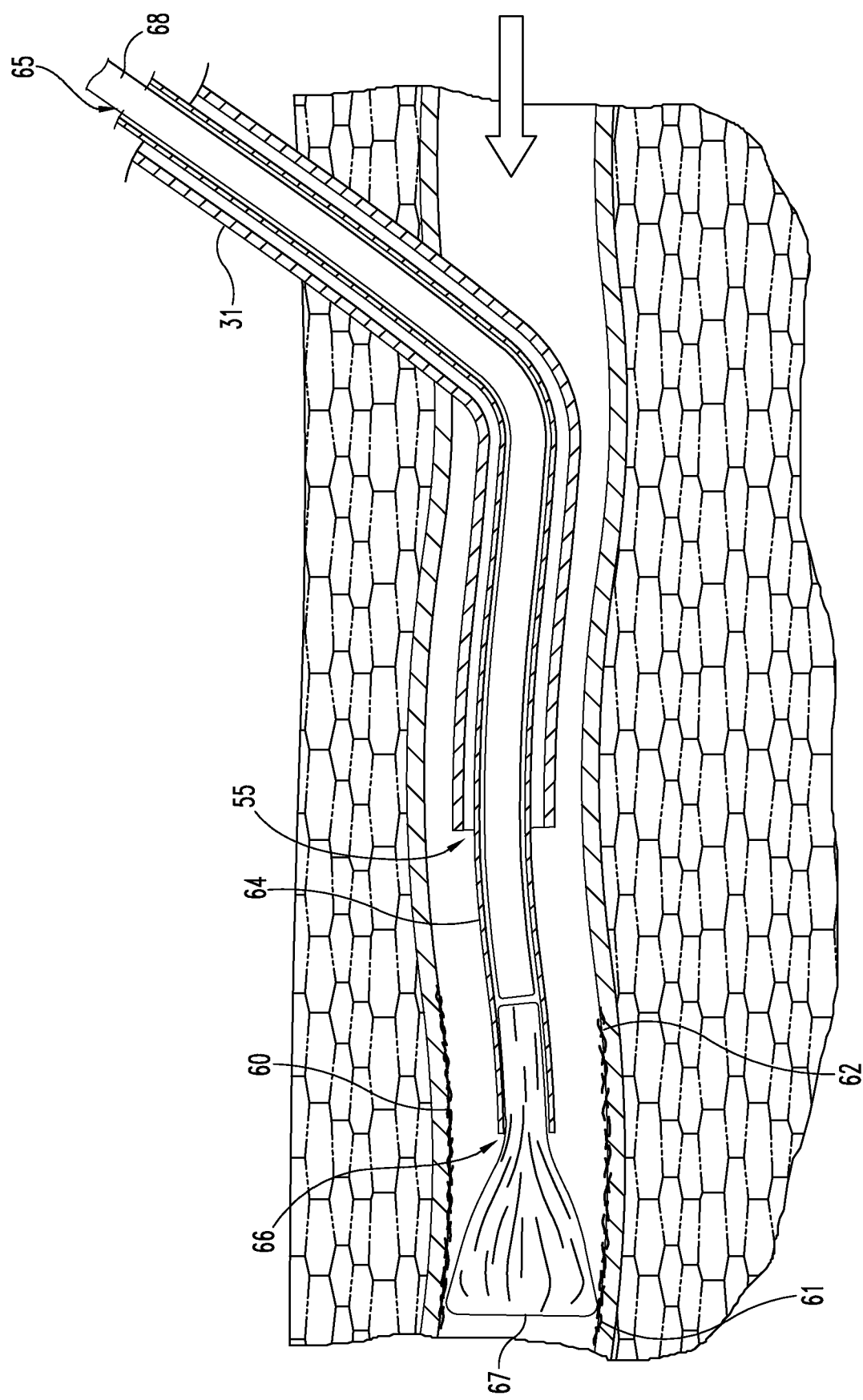
FIG. 5 shows a further illustrative use of the product of FIG. 4 incorporating an occluding member.

Referring now to FIG. 5, shown is a bodily vessel that includes an abraded region 60 extending generally between a first vessel location 61 and a second vessel location 62. The abrasion of the abraded region 60 of the bodily vessel can be caused as described above in relation to FIG. 4 or in another suitable manner as discussed herein or as will be apparent to one of ordinary skill in the art. In an illustrative method, with a sheath such as sheath 31 positioned in the vessel in the vicinity of abraded region 60, a catheter 64 or other endoluminally advanceable device is inserted into the sheath 31 and advanced therethrough until it exits the sheath 31 through its distal, open end 55. In a preferred form, catheter 64 has a lumen 65 or other interior region that is in communication with a distal opening 66 in catheter 64, and one or more occluding members 67 are removably positioned in lumen 65 for deployment through distal opening 66. An occluding member 67 can occupy any suitable volumetric shape, form, size, and material for causing a full or partial occlusion of a bodily passageway or other opening, and in this specific illustrative embodiment, a generally cylindrical occluding member is formed with a compressible material such as an extracellular matrix (ECM) sponge form material, although such members can be formed with a variety of sponge and non-sponge materials and/or devices as discussed herein.

Continuing with FIG. 5, when catheter 64 is desirably positioned in the vessel, occluding member 67 can be deployed from the catheter lumen 65 so that it expands in the vessel and contacts an abraded interior surface 60 of the vessel wall. Expansion of the member 67 can be facilitated by the presence of fluid in the vessel, e.g., patient blood, injected saline, etc., contacting the member either before, during, and/or after its deployment. In this particular embodiment, a pusher 68 extends through the catheter lumen 65 to assist in this process. Deployment can be achieved by holding the catheter 64 in place in the vessel and forcing the occluding member 67 out of the catheter lumen 65 with the pusher 68, by holding the pusher 68 steady and pulling back on the catheter 64, or a combination of the two, and in this regard, occluding members having various degrees of column strength can be utilized in the present disclosure to achieve a desirable deployment. When utilized, pushers and other similar translatable members might rely on simple contact to urge an implant from a delivery device lumen. Additionally or alternatively, a deployment member may be equipped to releasably attach to otherwise engage an occlusion device for moving the device with respect to the catheter, and potentially also for manipulating the occlusion device in the vascular vessel during and/or after deployment. Illustratively, a pusher may provide a mechanism by which to grasp or otherwise grip or capture part of an occlusion device, including but not limited to occluding member 67.

After the occluding member has been deployed, catheter 64 and outer sheath 31 can be removed from the vessel, leaving the occluding member behind in the vessel, e.g., extending along the entirety of abraded region 60. When working with an abraded region such as that shown in FIG. 5, one or more occluding member can be deployed so as to extend along any portion of the abraded region and/or beyond the region in one or both directions. Also, in an abraded region, abrasions might be continuous along a longitudinal wall segment as shown in FIG. 5, or they might be discontinuous. Lateral abrasions might be continuous or discontinuous around a vessel wall as well. In an alternative embodiment, one or more occluding members are inserted directly into sheath 31 for delivery into the vessel.

In this regard, occluding members that are pushable or guidable through a device lumen or a portion of a bodily vessel, e.g., implants comprising expandable foam pieces, layered constructs, etc. as discussed herein, will be utilized in certain forms of the present disclosure to achieve a desirable deployment. In some forms, occluding members can include an elongate foam or sponge cylinder or other member in a dried, compressed state, wherein the cylinder or other elongate member has sufficient column strength to be advanced on its own through a passageway by the application of force to the trailing end region of the member. In certain embodiments, the compressed material is effective to expand when wetted with water or other fluids, e.g., blood or other bodily fluids. Alternative such members can include a sheet material that is processed to itself such that it provides sufficient stiffness to the material to be advanceable through a vein or other bodily vessel, or a material that incorporates certain rigid or semi-rigid materials or objects that enhance the stiffness of the occlusive material to make the material guidable through a bodily lumen, if desired.

Suitable such implants can include occluding components that exhibit a column strength of at least about 200 kPA, for instance between about 200 kPA and about 12,000 kPA or more. In additional embodiments, an occluding member has a column strength of at least about 700 kPA, for example within the range of from about 700 kPA to about 11,000 kPA. Still additional devices can have column strengths from about 1,000 kPA to about 10,000 kPA, or from about 1,000 kPA to about 3,000 kPA. Such column strength values can be measured using a conventional Instron compressive strength testing machine. A sample of occlusive material, 5 cm in length, can be secured between to two test fixtures such that 0.5 cm of material is held within in each fixture. This test assembly results in a span of 4 cm of occlusive material between each fixture face. Thereafter, the fixtured sample can be placed in the Instron testing machine and compressed at a rate of 30 mm/min until the sample buckles. The force recorded at the point of buckling is the column strength or pushability number of the occlusive material.

In certain work performed to date, three segments of a dry small intestine submucosa foam material, each having a pre-compressed diameter of 16 mm and a length of 5 cm, were compressed down to a diameter of 4 mm using a radial compression device. Thereafter the column strength of each sample was individually determined using an Instron compressive strength testing machine. Each test was performed by securing 0.5 cm of each end of each sample within a test fixture such that a span of 4 cm of compressed foam material extended between the faces of the fixtures. The fixed sample was then compressed by the Instron machine at a rate of 30 mm/min and the compressive force was recorded. The compressive force at the point each test sample buckled was recorded as the column strength or pushability number for each sample. The column strengths for the foam samples were determined to be 1488.5 kPA, 1849.6 kPA, and 1628.8 kPA, respectively.

With certain implant designs, expansion and contact with the vessel wall can be sufficient to maintain the implant at a particular location in the vessel following deployment, although some implants useful in the disclosure will incorporate one or more anchoring or securement adaptations so as to mitigate undesirable migration of the device within the vessel. In some instances, a part of a device can embed itself in the vessel wall upon deployment and/or any subsequent repositioning of the device in the vessel. Any number of anchoring adaptations, barbs, hooks, ribs, adhesives, protuberances, and/or other suitable surface modifications can be incorporated into an inventive device to anchor and/or roughen, condition, or otherwise de-epithelialize at least a portion of the vessel wall during and/or after deployment of the device within the vessel. As discussed herein, the conditioning of the vessel wall tissue can serve to initiate a localized healing response in patient tissue that can be advantageous in enhancing the ingrowth of patient tissue into an inventive device, such as a device that is comprised of a tissue ingrowth receptive material.

In some aspects of the present disclosure, a single endoluminally advanceable component is effective to abrade an inner surface of a bodily vessel while providing an interior region for receiving one or more occluding members. One such component forms part of the medical product 80 depicted in FIG. 6. This product includes an endoluminally advanceable device 81 that has an abrading member 82 positioned about its distal end. The abrading member is configured to expand in a radially-outward fashion when no longer constrained within the catheter lumen, and includes a plurality of elongate arms having enlarged distal portions 83. Any portion of the abrading member can have an abrasive quality, and when the enlarged distal portions 83 are abrasive, they provide increased surface area for contacting and abrading the vessel wall 84. Device 81 further provides an interior region 85 that is suitable to house at least one occluding member 86 as shown. In this specific illustrative embodiment, the abrading member and the occluding member are cooperatively compressible so that they can be retracted within a lumen of a first sheath 88 to attain a relatively lower profile for delivery through the vasculature.

Figure 6:
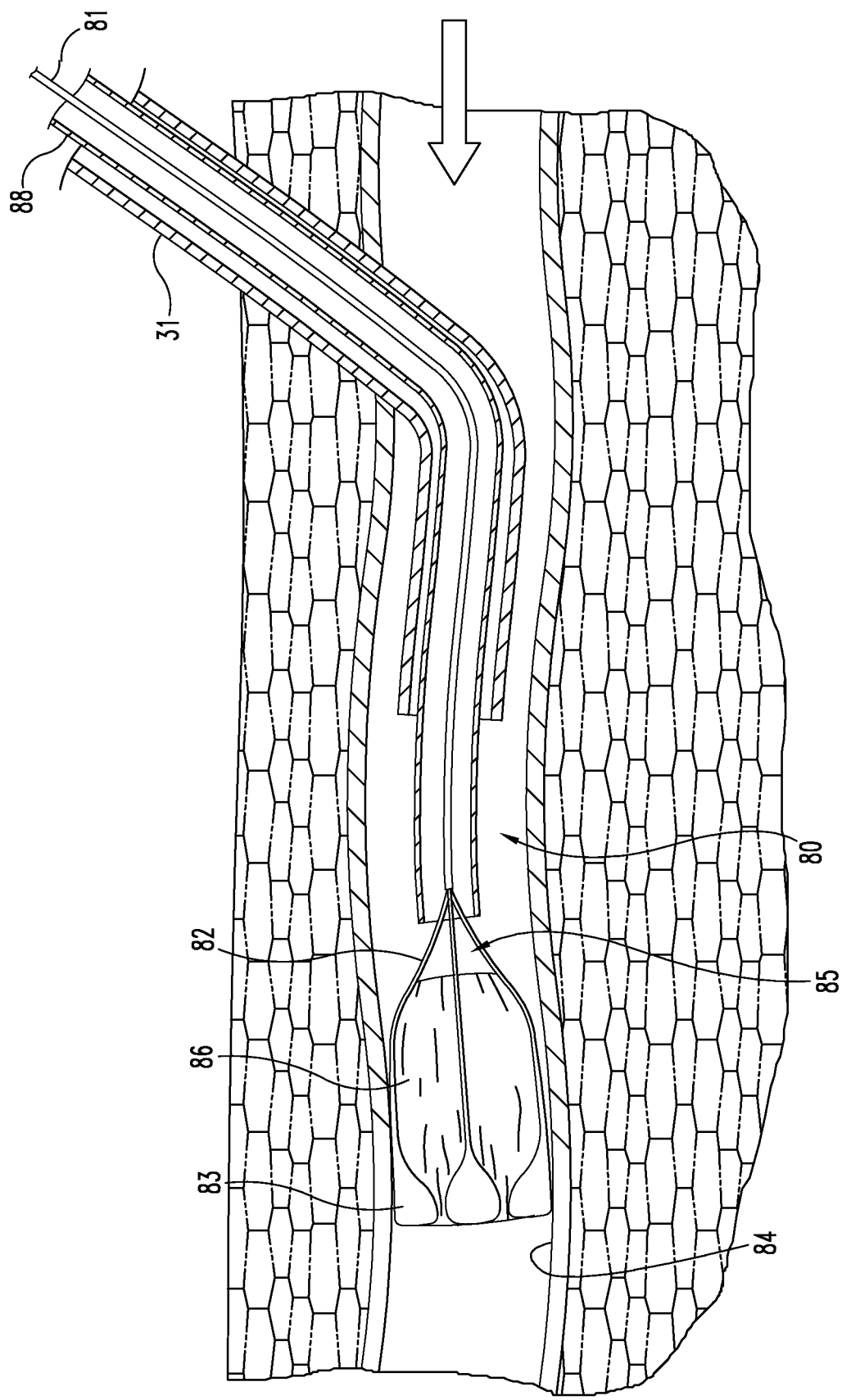
FIG. 6 shows another inventive product in a bodily vessel.

In an illustrative method, the abrading-occluding member combination is at least partially retracted within first sheath 88, and the first sheath is advanced through an emplaced, second sheath 31 until it exits the second sheath through its distal, open end. When desirably positioned in the vessel, the abrading-occluding member combination is deployed from sheath 88 causing the abrading member 82 to expand and contact the vessel wall 84 as shown in FIG. 6. In some forms, the abrading member will expand of its own accord with little or no help from the occluding member 86. In some other forms, the occluding member 86 will substantially force the abrading member against the vessel wall as it expands in the interior region of the abrading member. From this deployed condition, the occluding member can be further deployed from the abrading member interior before, after, or while the abrading member is being used to disrupt vessel surfaces. In this regard, some designs will incorporate a pusher to facilitate removal of the occluding member from abrading member interior, although other inventive embodiments will not require a pusher. In some embodiments, a portion of the occluding member will extend beyond and/or through the abrading member after initial deployment to contact the vessel wall. This contact, possibly aided by barbs or other anchoring adaptations, will be sufficient to maintain the general positioning of the occluding member in the vessel as the abrading member is withdrawn over the occluding member. As the abrading member is withdrawn, it leaves behind an abrasion which is then contacted by the occluding member that remains behind in the vessel.

Figure 7:
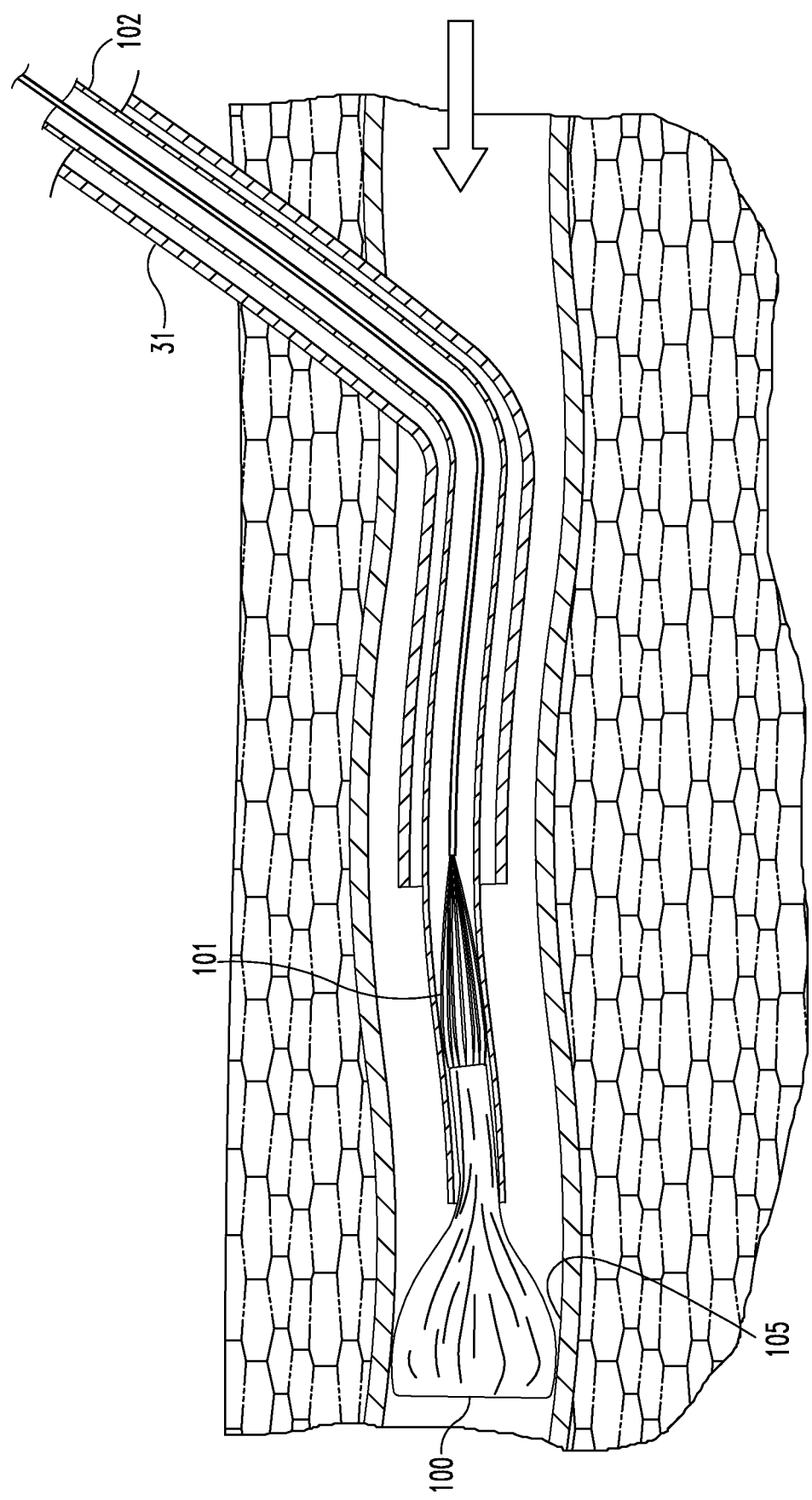
FIG. 7 shows yet another illustrative product in a bodily vessel.

In other inventive embodiments such as that shown in FIG. 7, an occluding member 100 and an abrading member 101 can be removably positioned in a first sheath 102 with at least part of the occluding member residing distally of the abrading member. In an illustrative method, these various components will be inserted into an emplaced, second sheath 31 and advanced therethrough until they exit the second sheath through its distal, open end. Thereafter, the occluding member can be deployed from the first sheath so that it expands and contacts an interior surface 105 of the bodily vessel as shown in FIG. 7. With this particular configuration, deployment can be achieved by holding the first sheath in place in the vessel and forcing the occluding member out of the first sheath lumen with the abrading member, by holding the abrading member steady and pulling back on the first sheath, or a combination of the two. Once the occluding member 100 and abrading member 101 are fully deployed in the vessel, they can be manipulated as discussed herein to disrupt the vessel wall and eventually leave the occluding member deployed in the vessel in and/or around a disrupted vessel wall region.

Figure 8:
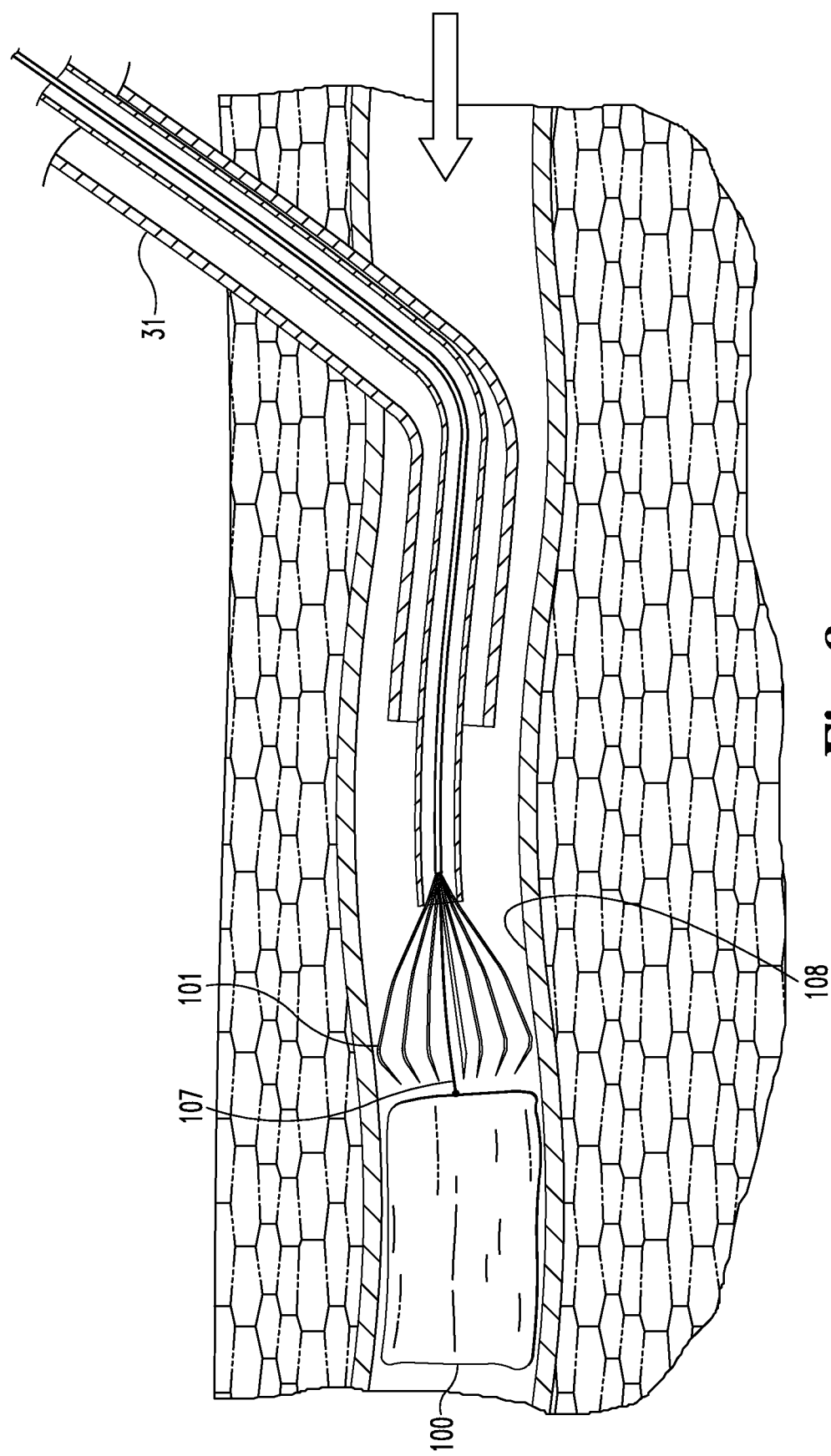
FIG. 8 shows the product of FIG. 7 with an optional coupling element.

FIG. 8 shows an adaptation of the previous embodiment in which an optional coupling element 107 is employed. In this specific illustrative embodiment, coupling element 107 is releasably attached to occluding member 100, and extends proximally from there to abrading member 101. Alternatively, a coupling element could extend between the occluding member and any other delivery component present in the vessel such as sheath 102 or sheath 31. This sort of coupling element might be effective to push an occluding member through a device lumen, bodily vessel, etc. if the coupling element and occluding member are pushable in this manner. As is the case with the illustrated design, a coupling element might also be effective to pull an occluding member through a vessel after it has been deployed. Thus, withdrawing the abrading member is effective to abrade an inner surface 108 of the vessel wall while simultaneously pulling the occluding member therealong and into contact with the abraded surface. Thereafter, the coupling element can be detached from the occluding member, and the various components can be removed from the vessel leaving occluding member 100 behind.

Coupling elements, when incorporated into an inventive device, can include any suitable adaptation to enable an occluding member and a delivery component to be temporarily connected or otherwise united with one another. These include but are not limited to those involving single- and multiple-part coupling mechanisms, grasping devices including lockable and non-lockable forceps, magnetic devices, energizable components, clasps, various bonding materials effective to bond two objects together, and combinations and variations thereof. In some preferred embodiments, a delivery device will include means for visualizing and identifying different device components and their surroundings during deployment.

Figure 9A:
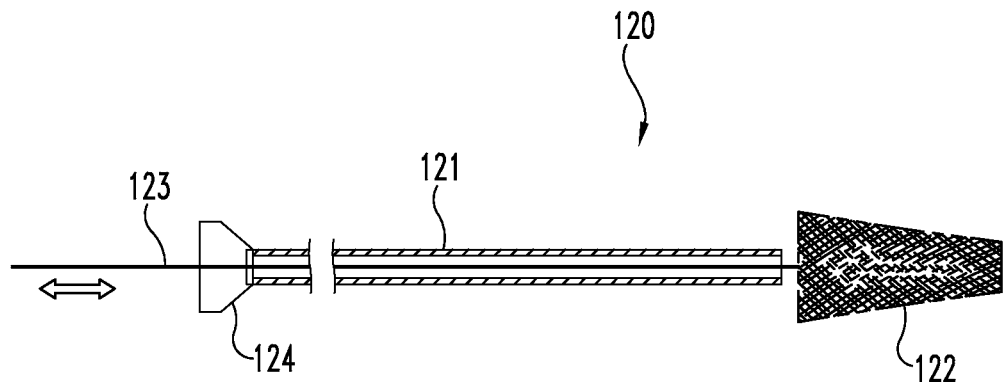
FIG. 9A is a partial view of an inventive medical product with an abrading member in a deployed condition.
Figure 9B:
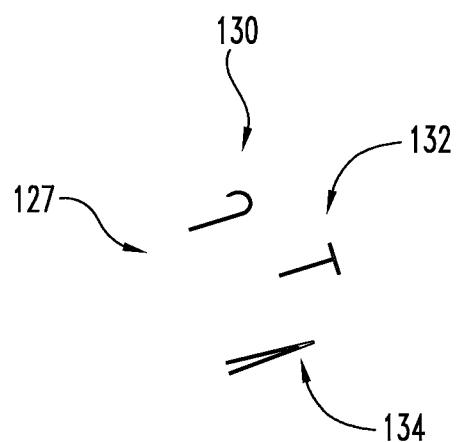
FIG. 9B illustrates optional portions of an abrading member.

Endoluminal components can be shaped and configured in a variety of ways for disrupting or otherwise modifying an interior surface of a bodily vessel. FIGS. 9A and 9B show another inventive product 120 with a retractable abrading component. This product includes a cannulated delivery device 121 having an optional hemostatic sealing system 124. An elongate member 123 extends through the delivery cannula, and provides an abrading member 122 about its distal end. The abrading member can occupy any suitable volumetric shape, form, size, and material, and in some embodiments, will be or include a brush-like member with micro-textured or other spines, a woven or braided component with abrasive qualities, a polymeric sleeve or sleeve-like member (e.g., a polymer tube filled with abrasive devices), or other suitable abrasive construct. As indicated by the arrow in FIG. 9A, elongate member 123 can be manipulated to retract and deploy the abrading member relative to the delivery cannula. Abrading member 122 is constrainable within the delivery device 121, and when deployed as shown in FIG. 9A, attains a larger profile with a maximum outer dimension, measured in the radial direction, greater than that of the portion of the delivery cannula extending through the vasculature of the patient. Preferably, the expanded condition of the abrading member is constructed and arranged for abrading an interior surface of a bodily vessel. The abrading member can be made abrasive in any suitable manner including by having a plurality of abrading adaptations 127 extend from and/or through a surface of the abrading member as shown in FIG. 9B. For example, in some instances, the abrading member comprises a brush with endothelial membrane surface traumatic ends, such as hooks 130, T-shaped members 132, and/or pointed members 134.

In additional embodiments, a catheter or other endoluminally advanceable device might include a convertible distal portion that can be caused to move outwardly toward an interior surface of a vessel wall when converted in the vessel. This outward movement, in some inventive devices, will be caused by compressing or expanding a distal component in a generally linear fashion, for example, in instances where an actuator is manipulated, e.g., pushed, pulled, twisted, etc., to cause a distal component to linearly compress and in turn expand.

Figure 10A:
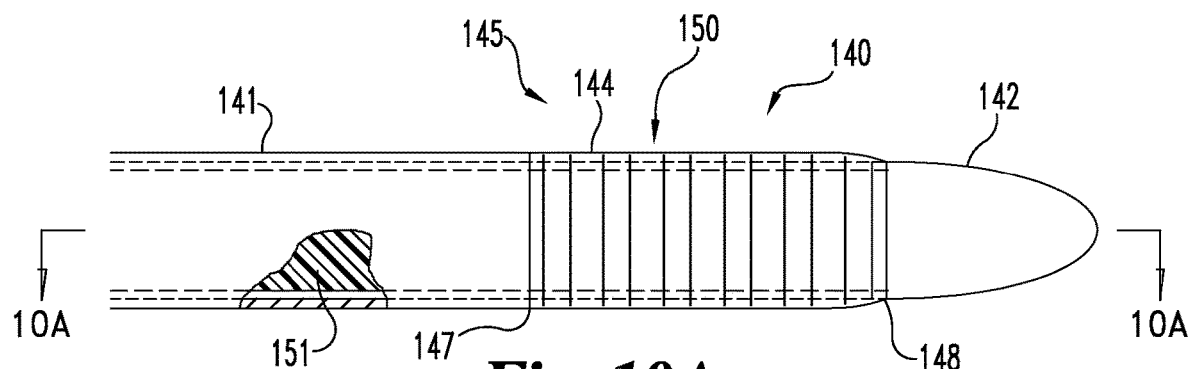
FIG. 10A is a partial view of an inventive medical product with an abrading member in a first condition.

Referring now to FIG. 10A, shown is a partial view of a medical product 140 according to another embodiment of the present disclosure. Medical product 140 includes a catheter 141 having a somewhat tapered and rounded distal end portion 142. A linearly compressible segment 144 occurs along a distal region 145 of the catheter, and although not necessary to broader aspects of the present disclosure, in this specific illustrative embodiment, segment 144 forms part of a wall of the catheter. Compressible segment 144 is substantially cylindrical, and has a first end 147, a second end 148 and an intermediate portion extending therebetween. Segment 144 is constructed such that compressing the segment in a generally linear fashion causes a portion 150 of the segment to move outwardly, e.g., in a generally radial fashion, upon operation of a translatable member 151 that is slidably received in a lumen of the catheter and is attached to a distal portion of the catheter, for example at or near the distal end of the linearly compressible segment. In an alternative embodiment that is largely similar to that shown in FIG. 10A, the translatable member extends beyond the compressible member to provide the distal end of the overall product, and the second end of the compressible member is attached to the translatable member proximate this distal end.

Translatable member 151, while being attached to a distal portion of the catheter, is able to move relative to other parts of the catheter, e.g., to slide back and forth within the catheter lumen. FIG. 10A shows linearly compressible segment 144 in a relatively lower-profile first condition for delivery through the vasculature. Segment 144 is constructed such that it will linearly compress when a sufficient pulling force is applied to member 151 to cause the member to slide through the catheter lumen in the direction of the arrow shown in FIG. 10B. As segment 144 linearly compresses, portion 150 will become outwardly displaced relative to its position in FIG. 10A. Accordingly, when the product is deployed in a bodily vessel, this displaced configuration can promote and/or facilitate a disruption of a vessel wall, for example, by placing portion 150 closer to or into contact with an interior surface of a vessel wall, displacing portion 150 radially outward, and then actuating catheter 141 by translational and/or rotational movement so as to drag portion 150 along the vessel wall.

Portion 150, and potentially other parts of the device, have an abrasive quality and can be made so in a variety of manners as discussed herein including by attaching abrasive particles or devices to the portion, by initially constructing the portion to have sharp edges and/or projections, by having objects project through an exterior surface of the portion, and/or in any other suitable manner. When moved against a vessel wall, these types of surface constructions, modifications, etc. are effective to roughen, condition, or otherwise de-epithelialize at least a portion of the wall. Optionally, the product can be adapted so that translatable member 151 can be locked in place relative to the catheter, for example, to lock the device in the conditions shown in FIGS. 10A and 10B or in other configurations.

Figure 10B:
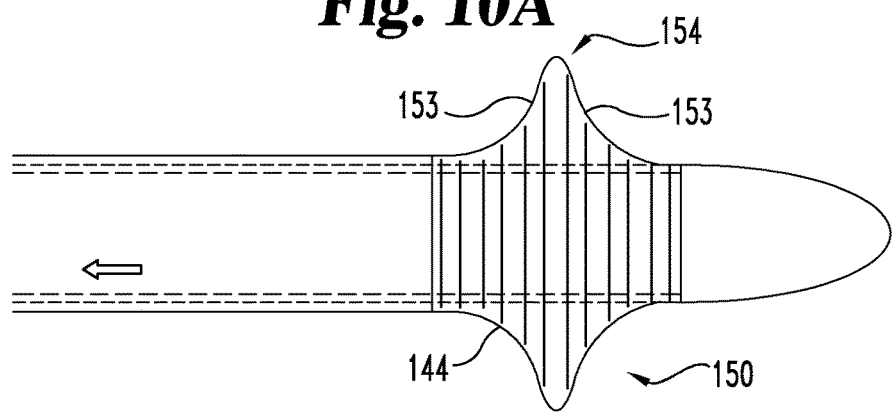
FIG. 10B shows the inventive product of FIG. 10A with the abrading member in a second condition.

In some instances, when linearly compressed and viewed from the side as shown in FIG. 10B, segment 144 has opposing arc surfaces 153 providing a single curved peak 154. For example, as shown in FIG. 10B, the outwardly displaceable portion 150 has an outer surface having a concave portion 153 and a convex portion 154. The concave portion has a length along a longitudinal axis of the outwardly displaceable portion and the convex portion has a length along the longitudinal axis and, as shown in FIG. 10B, the length of the concave portion can be greater than the length of the convex portion. Contact with the vessel wall will generally occur in the vicinity of this peak. If linearly compressed and viewed from the front, the first end 147 and second end 148 of the segment would have a first circumference, and parts of the segment including peak 154 would have a second, larger circumference. This larger circumference, in some configurations, would be the same or close to the circumference of the inner vessel wall.

Deformable endoluminal components such as segment 144 can exhibit a variety of shapes and sizes before and after being deformed. Accordingly, segment 144 could be adapted to have a differently shaped peak, multiple peaks and/or other non-peak projections when linearly compressed and viewed from the side. When there is a change in circumference along a particular length of a component, this change may or may not be constant. Thus, while segment 144 has opposing arc surfaces when compressed and viewed from the side, it could be adapted to have a variety of other suitably shaped surfaces as well, for example, some having arced or other similar curvilinear surfaces of varying dimensions, as well as some having non-curvilinear surfaces (e.g., linear surfaces) when viewed from the side. In this regard, a deformable component, or any portion thereof, can exhibit a generally cylindrical shape, a convex shape, a concave shape, a conical shape or any other suitable shape including some that have tapered and/or non-tapered longitudinal portions. As well, when viewed from the front, an outwardly displaced portion can exhibit a variety shapes including some that have rectilinear and/or curvilinear features. These include but are not limited to generally circular and non-circular (e.g., elliptical, square, star-shaped, triangular, hexagonal, etc.) shapes.

A wall of an abrading member or other endoluminal component can incorporate one or more adaptations for promoting and/or facilitating an outward displacement of a portion of the wall. Illustratively, a wall can incorporate scores, thinner portions, and other openings and non-openings that weaken structurally a portion of the wall to facilitate an outward displacement. Such adaptations may involve any suitable means for facilitating movement of a wall portion. In certain beneficial forms, a wall segment will be controllably movable with regard to a particular grouping of weakened portions along the wall. These types of adaptations can be incorporated into a wall in a variety of ways as will be appreciated by those skilled in the art. Illustratively, a wall segment, in certain embodiments, can be originally formed (e.g., in a mold, extruded, etc.) with weakened portions already incorporated into the segment. When formed in an existing wall segment, weakened portions or other similar adaptations can be formed using a variety of techniques and instruments, for example, using lasers such as in laser etching, or employing any number of other tools or instruments. Forming these types of adaptations may or may not involve removing or otherwise eliminating portions of the wall material. Other suitable wall adaptations can be or include joints, hinges, flexible and non-flexible connectors, bendable portions, and/or device constructions that involve the use of multiple materials and/or differential material properties in selected regions of an abrading member.

Figure 11A:
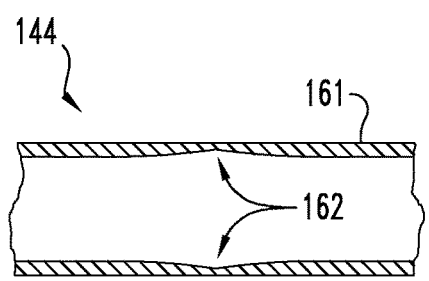
FIG. 11A provides a partial, cross-sectional view of the abrading member of FIG. 10A along the view line 10A-10A shown in FIG. 10A.
Figure 11B:
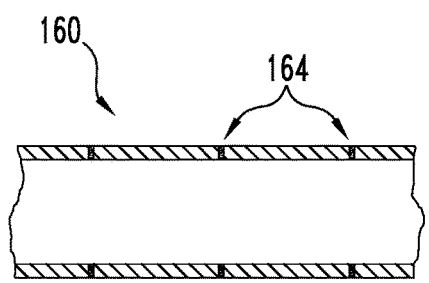
FIG. 11B provides a partial, cross-sectional view of an abrading member according to another embodiment of the present disclosure.

Turning now to FIG. 11A, shown is a partial, cross-sectional view of the linearly compressible segment 144 of catheter 141 of FIG. 10A in a low-profile condition. Segment 144 includes a generally cylindrical wall 161. To promote and/or facilitate a generally controlled outward movement of portion 150, the wall includes a weakened region 162 that extends around the segment in a generally annular fashion. When sufficient axially compressive force is applied to one or both ends of the member, the weakened region will help control an outward displacement of the wall as generally shown in FIG. 10B. An alternative device configuration is shown in FIG. 11B where a compressible segment 160 includes a wall having multiple joints 164 to assist in an outward displacement of the wall. Illustratively, the centrally-located joint might tend to bend in a first direction, while the flanking joints might tend to bend in a generally opposite direction when the segment is compressed in a direction along the longitudinal axis of segment 160.

Figure 12A:
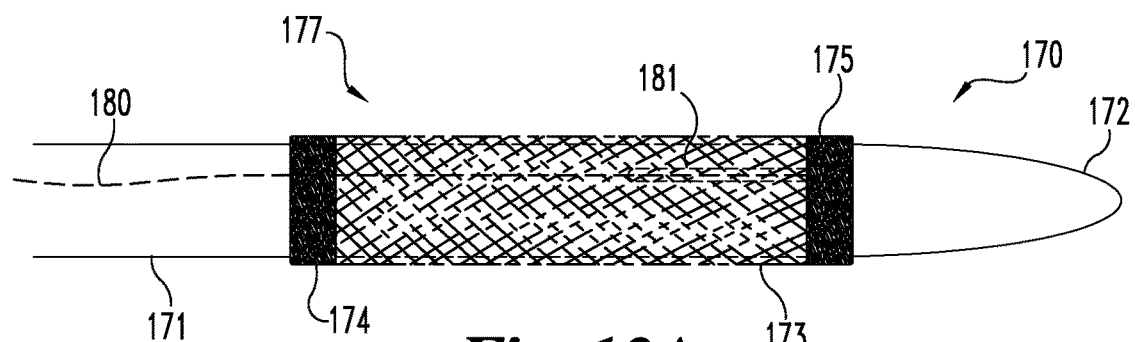
FIG. 12A is a partial view of an inventive medical product with an abrading member in a first condition.
Figure 12B:
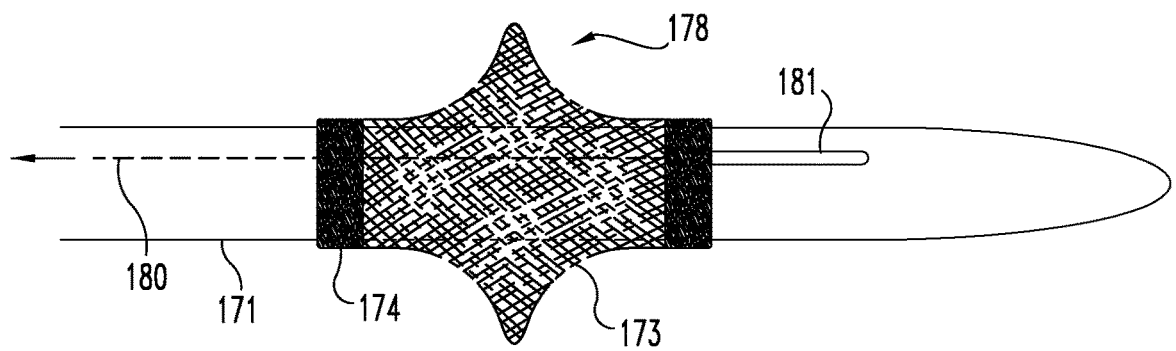
FIG. 12B shows the inventive product of FIG. 12A with the abrading member in a second condition.

Referring now to FIG. 12A, shown is a partial view of another inventive product 170 in a delivery configuration. Product 170 includes a catheter 171 having a dome-shaped tip 172. A linearly-compressible segment 173 is received over the catheter. Compressible segment 173 has a first end 174 and a second end 175. Segment 173 is positioned along a distal region 177 of the catheter 171, with its first end 174 affixed to the catheter 171. Segment 173 is constructed such that compressing the segment in a generally linear fashion causes a portion 178 of the segment 173 to move outwardly. An elongate pulling member, such as a rod, cable, or wire 180 is received in an interior region of the catheter 171, and extends through an elongate slot 181 in a wall of the catheter 171 to attach to the compressible segment 173, for example, at its distal end. As shown in FIG. 12B, sufficiently pulling the wire 180 through the catheter 171, such as in the direction of the arrow shown, is effective to linearly compress segment 173 and thereby cause portion 178 to become outwardly displaced relative to its position in FIG. 12A. As segment 173 compresses, wire 180 slides along slot in a distal to proximal direction. As described above, segment 173 can have an abrasive exterior surface and/or is otherwise configured to abrade an interior surface of a bodily vessel wall when moved against the wall.

Figure 13A:
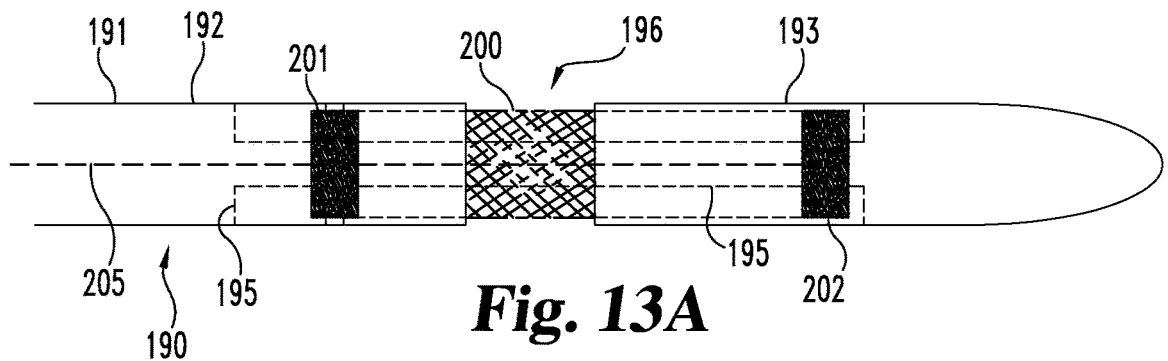
FIG. 13A is a partial view of an inventive medical product with an abrading member in a first condition.
Figure 13B:
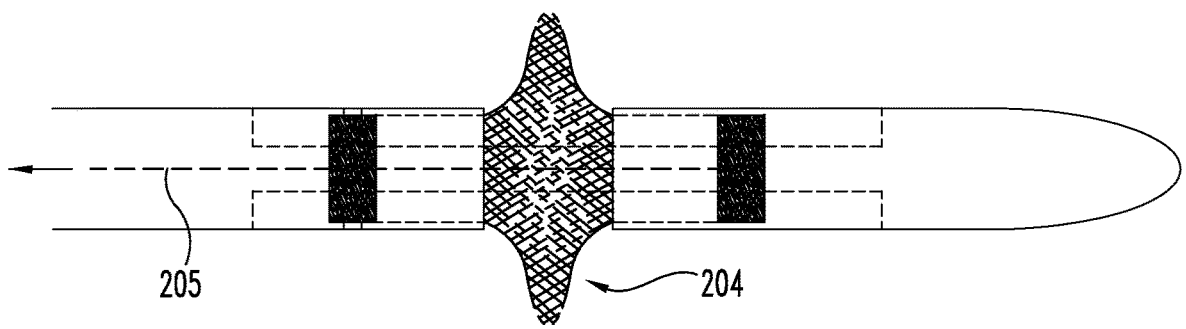
FIG. 13B shows the inventive product of FIG. 13A with the abrading member in a second condition.

FIG. 13A shows another inventive product 190 in a delivery configuration. Product 190 includes an endoluminally advanceable device 191 having a first cannulated portion 192 and a second cannulated portion 193. Frame segments 195 extend within and between the cannulated portions, and are connected to both cannulated portions to provide an open side region 196 in the device. A linearly compressible segment 200 also extends within and between the cannulated portions 192, 193; and is additionally received over frame segments 195. Segment 200 has a first end 201 that is received within and fixedly attached to first cannulated portion 192, and a second end 202 that can slide freely back and forth within second cannulated portion 193. Segment 200 is constructed such that compressing the segment 200 in a generally linear fashion causes a portion 204 of the segment 200 to move outwardly and through or further through open side region 196. A wire or rod 205 extends through the segment 200 and cannulated portions 192, 193; and is attached to the segment 200 at or near its distal end (e.g., second end 202). Sufficiently pulling the wire or rod 205 through the device 191, such as in the direction of the arrow shown in FIG. 13B, is effective to linearly compress segment 200 along its longitudinal axis and thereby cause portion 204 to move outwardly relative to its position in FIG. 13A. Segment 200 has an abrasive exterior surface and/or is otherwise configured to abrade an interior surface of a bodily vessel wall when moved against the wall.

Figure 14:
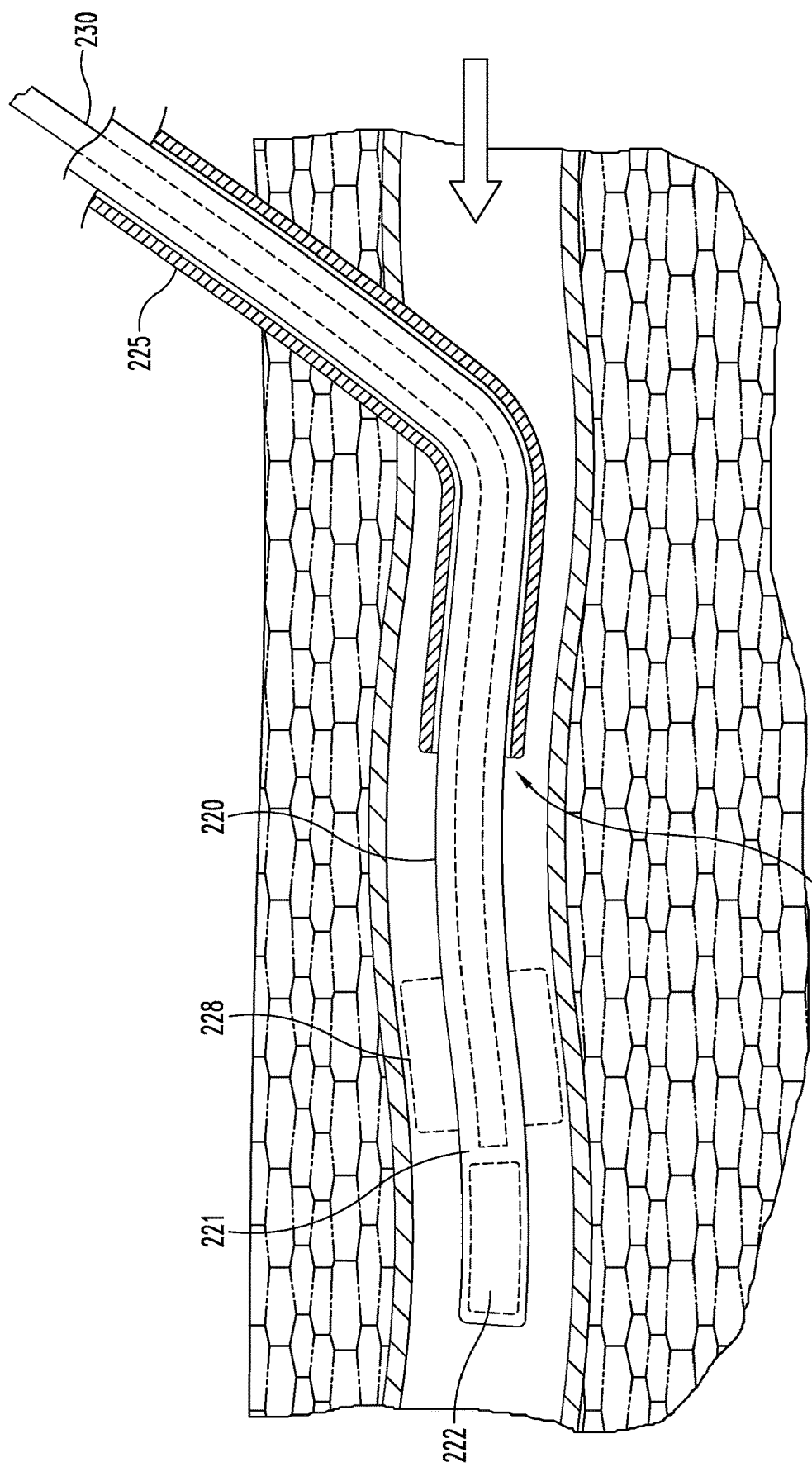
FIG. 14 shows another inventive product positioned in a bodily vessel.

FIG. 14 shows another inventive product that incorporates an endoluminally advanceable member 220 that is effective to abrade an inner surface of a bodily vessel while providing an interior region 221 for receiving one or more occluding members 222. In an illustrative method, the distal end of member 220 is inserted into an emplaced sheath 225 and advanced therethrough until it exits the sheath through the sheath distal end 226. In the vessel, an outwardly displaceable portion 228 can be caused or allowed to move outwardly toward a vessel wall surface for contacting and abrading that surface. Outwardly displaceable portion 228 is shown in phantom in FIG. 14, and can be or include any of the outwardly displaceable components described herein and/or those otherwise known in the art for contacting vessel walls, for example, those that involve balloons or expandable structures. In some embodiments, an abrading step will be carried out first, and then occluding member 222 will be deployed from the interior region (e.g., using an optional pushing device such as pusher 230) and into contact with the vessel wall at or near an abraded region. In other embodiments, occluding member 222 will be deployed before or simultaneously with an abrasion of the vessel wall. Thereafter, member 220 can be configured for removal from the vessel, and both the member 220 and sheath 225 can be withdrawn leaving one or more occluding members behind.

Endoluminally advanceable devices useful in the disclosure (e.g., any of the above mentioned sheaths and/or catheters, guidewires, endoscopes, etc.) can be shaped and configured in a variety of manners. A device might be constructed to traverse a body passageway without buckling or kinking or causing unacceptable damage to soft tissues defining the passageway. In some forms, the distal end of a device, or a portion thereof, will be particularly configured to avoid substantially cutting or tearing surrounding soft tissues or otherwise enhance its travel through body passageways. For example, a device distal end can include a tapered portion and/or have a dome-shaped or otherwise rounded tip. Selected portions of a device (e.g., the distal end), might be rigid, malleable, semi-flexible, or flexible. In certain embodiments, an endoluminally advanceable device is particularly adapted for moving through and into body passages that angulate sharply or curve abruptly. In some of these embodiments, the device is configured to be directable or steerable through the passageway, and therefore, exhibits desirable characteristics, e.g., sufficient stiffness, to allow an operator to apply an adequate degree of ante-grade force to the device to allow it to traverse a passageway in a desirable manner. In some forms, a device will be somewhat rigid in terms of column strength, yet will be equipped with one or more reliefs, indentations, thinner portions, or other similar adaptations along the device to provide some lateral flexibility to the device. Additionally or alternatively, a device may incorporate a mechanism of some sort that enables an operator to steer or otherwise navigate the device through a tortuous body passageway. These and other adaptations for facilitating advancement of a device through a body passageway will be recognized by those skilled in the art, and therefore, are encompassed by the present disclosure. In some aspects, components for visualizing and/or irrigating a body passageway can be received within an endoluminally advanceable device lumen as discussed herein.

Any of the above mentioned sheaths and/or catheters, dilators, endoluminal deployment devices, such as pushers, wire guides and needles used in the present disclosure can all be conventional marketed products or modifications thereof. For example, sheaths can be formed from PTFE (e.g., Teflon) or polyamide (e.g., Nylon) material, or a combination of materials such as an assembly including an inner layer of PTFE, a flat wire coil over the PTFE for kink resistance, and a polyamide (Nylon) outer layer to provide integrity to the overall structure and a smooth surface (e.g. as in the Flexor sheath, Cook, Inc.). Dilators and pushers can be made from conventional dilator/catheter/pusher type materials such as polyethylene, polyamide, polyurethane or vinyl, stainless steel, or any combination of these materials. Fittings provided for sheath/dilator assemblies can be conventional elements such as luer locks, and the dilator can have a fitting allowing it to be locked to the sheath during insertion and manipulation. Catheters and other inventive components can be made from conventional materials such as polyethylene, polyamide, PTFE, polyurethane, and other materials.

As is known, the distal ends, or any desirable segment or portion, of the catheters, sheaths, dilators, wires or other components, such as occlusive devices, used in percutaneous procedures can include markers that can be X-ray, sonographically, or otherwise non-invasively visualized to identify their location during the procedure. Metallic bands of stainless steel, tantalum, platinum, gold, or other suitable materials, which include a dimple pattern, can serve the purpose for both ultrasound and X-ray identification. As well, distal and/or proximal ends and/or other locations on occluder devices may include markers for non-invasive imaging, including imageable materials such as those discussed above as well as substances that can be incorporated into occluding materials, e.g., radiopaque elements such as but not limited to a radiopaque coating, attached radiopaque object, or integrated radiopaque substance. Any suitable radiopaque substance, including but not limited to, tantalum such as tantalum powder, can be incorporated into a medical product of the present disclosure. Other radiopaque materials comprise bismuth, iodine, and barium, as well as other suitable markers.

Additionally, components for irrigating a body passageway can be received within an endoluminally advanceable device lumen. Illustratively, such components, as well as other desirable instruments and/or materials, can be passed into the proximal end of the device lumen (or alternatively, can be passed into one or more openings in a sidewall of the device), and through at least a portion of the device lumen. For example, in certain aspects, a device of the present disclosure includes one or more ports in a sidewall thereof, wherein each port can be associated with a corresponding channel that extends from the port toward the distal end of the device. In some forms, one or more port and channel combinations are each configured to receive one or more instruments and/or materials therethrough. For example, a port can be configured to receive one or more optical fibers for visualization and/or illumination of a body passageway and surrounding soft tissues, for example, fiber-optic bundles including a plurality of glass fibers comprised of silicone, silicone dioxide, and/or a suitable equivalent.

Device ports can also be configured to receive fluids for irrigation of a body passageway. Such fluids can be provided from an external bag of fluid that is connected to the port of the irrigation channel by means of flexible tubing. If necessary, the fluid can be infused under pressure using a pressure bag applied to the fluid source, to increase the pressure under which the fluid is infused. Suitable device ports can further be configured to receive guide-wires, drains, solutions such as sealants or sclerosants, high intensity light sources, a lever system to steer the device (e.g., wherein the device and/or its distal tip is directable in one, two, or three planes), and/or any other suitable instruments and/or materials. In some forms, a device port is configured to receive an optical viewing and lens system that may be attached to a video camera, a video monitor, and a video recorder for viewing at the distal end of the device.

Turning now to a discussion of occlusive implant materials useful for any of the occluding members and some abrading members discussed herein, such materials can include any suitable biocompatible material. Generally, the occlusion materials may include synthetic materials or reconstituted or naturally-derived collagenous materials. Thus, inventive devices can utilize one or more of a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

As well, the disclosed occluding members can incorporate biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Biocompatible materials that are at least bioresorbable will provide advantage in certain embodiments of the present disclosure, with materials that are bioremodelable and promote cellular invasion and ingrowth providing particular advantage. Illustratively, remodelable materials may be used in this context to promote cellular growth within the occlusive materials (e.g., the occluding member) to promote the closure of an occluded passageway.

Bioremodelable materials of the present disclosure can be provided by collagenous extracellular matrix (ECM) materials possessing biotropic properties, including in certain forms angiogenic collagenous ECM materials. For example, suitable collagenous materials include ECM materials, such as submucosa, renal capsule membrane, dermal collagen, dura mater, pericardium, serosa, facia lata, peritoneum, or basement membrane layers including liver basement membrane. The preferred medical graft products of the present disclosure will include submucosa, such as submucosa derived from a warm-blooded vertebrate. Suitable submucosa materials for these purposes include, for instance, intestinal submucosa, including small intestinal submucosa, stomach submucosa, urinary bladder submucosa, and uterine submucosa. Mammalian submucosa materials are preferred. In particular, submucosa materials derived from animals raised for meat or other product production, e.g. pigs, cattle or sheep, will be advantageous. Porcine submucosa provides a particularly preferred material for use in the present disclosure, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in the present disclosure can be obtained by harvesting such tissue sources and delaminating the submucosa from smooth muscle layers, mucosal layers, and/or other layers occurring in the tissue source. For additional information concerning submucosa useful in certain embodiments of the present disclosure, and its isolation and treatment, reference can be made, for example, to U.S. Pat. Nos. 4,902,508, 5,554,389, 5,993,844, 6,206,931, and 6,099,567.

Submucosa or other ECM materials can be derived from any suitable organ or other tissue source, usually sources containing connective tissues. The ECM materials processed for use in certain embodiments will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in embodiments of the present disclosure will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the present disclosure.

The submucosa or other ECM material used in illustrative embodiments may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

As prepared and used, the submucosa material or any other ECM material may optionally retain and/or include growth factors or other bioactive components native to the source tissue. For example, the submucosa or other ECM material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in embodiments of the present disclosure may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression. In certain preferred embodiments of the present disclosure, the ECM material will exhibit the capacity to promote angiogenesis.

Further, in addition or as an alternative to the inclusion of native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the ECM material within the patient.

Submucosa or other ECM material used in embodiments of the present disclosure is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in embodiments of the present disclosure is preferably disinfected with an oxidizing agent, particularly a peracid, such as peracetic acid. These and additional properties of submucosa or other ECM materials taught in U.S. Pat. No. 6,206,931 may be characteristic of the submucosa used in aspects of the present disclosure.

In certain aspects, the present disclosure utilizes an occluding member that includes a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another. Using multilaminate materials can add to the column strength of an implant, or a portion thereof.

A variety of dehydration-induced bonding methods can be used to fuse ECM portions of the bioremodelable material. In one preferred embodiment, the multiple layers of ECM material are compressed under dehydrating conditions. The term "dehydrating conditions" can include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressing surfaces. One particularly useful method of dehydration bonding ECM materials is lyophilization, e.g. freeze-drying or evaporative cooling conditions.

Another method of dehydration bonding comprises pulling a vacuum on the assembly while simultaneously pressing the assembly together. This method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is sometimes advantageous to perform drying operations under relatively mild temperature exposure conditions that minimize deleterious effects upon the ECM materials of the present disclosure, for example native collagen structures and potentially bioactive substances present. Thus, drying operations conducted with no or substantially no duration of exposure to temperatures above human body temperature or slightly higher, say, no higher than about 38° C., will preferably be used in some forms of the present disclosure. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Turning now to a discussion of three-dimensionally stable materials that can be formed into occlusive constructs (e.g., occluding members) for use in aspects of the present disclosure, such materials may include any suitable biocompatible sponge or foam material. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the present disclosure will comprise collagen as a matrix-forming material, either alone or in combination with one or more other matrix forming materials. In general, sponge matrices useful in embodiments of the present disclosure can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collageneous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. In preferred embodiments of the present disclosure, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the present disclosure will have from 2 to about 10 epoxide groups per molecule. The use of such epoxides and/or other crosslinking agents which impart polar groups and a hydrophilic character to the resulting matrix will provide for good wetability and rapid hydration and expansion of closure devices of the present disclosure.

Preferred sources of collagen for forming sponge matrices include extracellular matrix materials as discussed above, such as collagenous submucosal tissues, and other collagenous basement membrane materials. These include, for example, small intestinal submucosa, stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials can be highly expandable when wetted, so as to achieve an expanded configuration. Illustratively, expandable sponge materials can exhibit the capacity to expand at least 100% by volume, more preferably at least about 200% by volume, and typically in the range of about 300% by volume to about 1000% by volume, when wetted to saturation with deionized water. Sponge materials used in the present disclosure can also exhibit advantageous rates of expansion, achieving volume expansions as noted above in less than about 10 seconds, more preferably less than about 5 seconds, when immersed in deionized water.

Highly compact, dense sponge matrices can be prepared by first hydrating or otherwise wetting a porous sponge matrix, and then compressing and drying the element. Such preparative processes generally provide a denser, rigid and stably compressed sponge matrix than processes such as simple compaction of the dry sponge matrix. Drying can be conducted sufficiently to stabilize the sponge matrix. For example, preferred drying procedures will reduce the liquid (e.g. water) content of the matrix to less than about 20% by weight, more preferably less than about 10% by weight. Compression forces can be applied so as to achieve a final density and/or desirable configuration, and can be applied in one, two or three dimensions, including radially. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Compressed sponge matrices forming occlusive bodies (e.g., occluding members) can be highly dense, typically having densities of at least about 0.05 g/cm3, preferably in the range of about 0.05 g/cm3 to about 0.2 g/cm3, and more preferably about 0.075 g/cm3 to about 0.2 g/cm3. The compacted sponge matrix can have sufficient rigidity to be deployed by passage through bodily vessels, needles, catheters or sheaths, such as by utilizing a push rod or other pusher element to force the sponge matrix body through the needle and/or catheter cannula for example. Expanded sponge densities (dry) will generally be less than the corresponding compacted densities. Typical expanded densities (dry) will range from about 0.01 g/cm3 to about 0.1 g/cm3, more preferably about 0.02 g/cm3 to about 0.07 g/cm3.

Compressed sponge materials may also contain agents which promote further retention of the compressed, high density form of the matrices. These may include for example starch, cellulose, sugars such as dextrose, or glycerin. Such agents can optionally be included in the liquid (preferably aqueous) used to hydrate or otherwise wet the sponge prior to compaction and drying. For additional information concerning foam or sponge form materials that can be useful in embodiments of the present disclosure, reference can be made, for example, to U.S. Pat. App. Pub. No. 2003/0013989.

In additional embodiments, occlusion devices of the present disclosure, such as any of the occluding members discussed herein, can be made from ECMs or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a bodily segment within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECMs. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of three-dimensionally stable shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Expanded collagenous materials can be used to prepare a wide variety of occlusive devices, such as the occluding members disclosed herein. Methods for preparing such occlusive devices can include contacting an ECM or other collagenous starting material with an alkaline substance in an amount effective to expand the material, casting or otherwise forming the expanded collagenous material into an occlusive shape (e.g. an elongate tube or cylinder), and lyophilizing the expanded material to form a dried occlusive device.

When utilized, implantable devices can be any suitable length and will generally be of sufficient dimension to achieve occlusion of the desired stretch of vascular vessel, either alone or in combination with other similar or differing devices. In certain embodiments, a device, in implanted form, will have a length of at least about 0.4 cm, and in many situations will have a length ranging from about 1 cm to about 30 cm, more typically from about 2 cm to about 15 cm. Indeed, for preferred occlusion procedures involving a significant stretch of an artery or vein, one or more occlusion devices (e.g., occluding members) having a total length greater than 30 cm will be used. Illustratively, in the occlusion of the greater saphenous vein in human adolescents or adults, one or more occlusion devices having a total length of at least about 40 cm or 50 cm can be used.

While discussions above focus upon occluding the greater saphenous vein via access at the knee level, the greater saphenous vein may also be accessed at a lower level, e.g., near the ankle. During such access, any or all of the saphenous vein occurring between the ankle and the sapheno-femoral junction may be subjected to occlusion. Other veins in the leg(s) that may be involved in the varicose vein condition may also be occluded, alternatively or in addition to the greater saphenous vein. For example, the lesser saphenous vein, or varicose veins themselves, may be occluded and obliterated in accordance with the present disclosure. Further, other veins or arteries in the leg(s) or elsewhere in the body may be occluded within the scope of the present disclosure.

In additional embodiments, the present disclosure provides medical products that include means or devices as described herein for delivering vascular implants into and otherwise providing occlusion in the vasculature, and written materials including instructions for use of the means or devices to deliver vascular implants into and otherwise provide occlusion in the vasculature. The products can include the means or devices packaged together with the instructions, e.g., in sterile medical packaging. Related embodiments of the present disclosure include methods for distributing such means or devices, or otherwise conducting business, which include distributing such means or devices for delivering vascular implants into and otherwise providing occlusion in the vasculature, and also distributing information relating the use of such means or devices for delivering vascular implants into and otherwise providing occlusion in the vasculature. Such information can be distributed packaged with the means or device, or separately, e.g. including information or instructions available on a communication network, including a global computer communication network such as the internet.

The present disclosure also provides, in certain aspects, a line of medical products, wherein a medical product of the present disclosure includes one or more devices, apparatuses or systems of the present disclosure in a sealed package. In some forms of the present disclosure, medical products are provided that include one or more occlusion devices such as any of those described herein, and potentially also a suitable delivery apparatus or other delivery instrumentation, enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

Additionally, the package can include indicia to communicate the contents of the package to a person, machine, computer, and/or electronic device. Such indicia may include the dimensions of, the type of materials used to form, and/or other useful information regarding the contents of the package. In certain embodiments, the contents are packaged for sale with instructions for use. For example, in certain preferred embodiments, a medical product includes at least one occlusion device and delivery instrumentation sealed within a sterile package, wherein the packaging can have visible indicia identifying the contents as suitable for providing occlusion in the vasculature, and/or can contain or otherwise be associated with printed materials identifying the contents as such and including information concerning their use.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present disclosure, and is not intended to limit the present disclosure in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A medical product for abrading an interior surface of a vascular vessel, the medical product comprising:
    an endoluminally advanceable device comprising a linearly compressible segment positioned along a distal region of said device, said linearly compressible segment having a longitudinal axis, a first end, a second end, and an intermediate region occurring between said first end and said second end, said intermediate region comprising an outwardly displaceable portion configured to move outwardly toward the interior surface of the vascular vessel when said compressible segment is linearly compressed in the vessel;
    said outwardly displaceable portion including one or more abrasive adaptations arranged to abrade the interior surface of the vascular vessel; and
    an actuating member coupled to said compressible segment and actuatable to linearly compress said compressible segment in the vessel;
    wherein said outwardly displaceable portion has a rough exterior surface relative to other portions of the endoluminally advanceable device;
    wherein in an outwardly displaced configuration said outwardly displaceable portion has an outer surface having a first concave portion, a second concave portion, and a convex portion extending from the first concave portion to the second concave portion;
    wherein said first concave portion has a length along said longitudinal axis and said convex portion has a length along said longitudinal axis;
    wherein said length of said first concave portion is greater than said length of said convex portion; and
    wherein said linearly compressible segment includes weakened portions including a plurality of joints extending along the longitudinal axis of the intermediate region of the linearly compressible segment.

2. The medical product of claim 1, wherein said linearly compressible segment comprises a longitudinal wall segment of said distal region of said endoluminally advanceable device.

3. The medical product of claim 1, wherein said endoluminally advanceable device has an interior surface that defines a lumen.

4. The medical product of claim 3, wherein said actuating member is slidably received in said lumen.

5. The medical product of claim 1, wherein said convex portion defines a curved peak and said curved peak is positioned between curved concave portions.

6. The medical product of claim 1, wherein the actuating member is coupled to said second end of said compressible segment and actuatable relative to the first end to linearly compress said compressible segment in the vessel.

7. A medical product for abrading an interior surface of a vascular vessel, the medical product comprising:
- an endoluminally advanceable device comprising a linearly compressible segment positioned along a distal region of said device, said linearly compressible segment having a longitudinal axis, a first end, a second end, and an intermediate region occurring between said first end and said second end, said intermediate region comprising an outwardly displaceable portion;
- said outwardly displaceable portion including one or more abrasive adaptations effective to de-epithelialize at least a portion of a vessel wall when dragged against the vessel wall; and
- an actuating member coupled to and extending proximally from said compressible segment and linearly actuatable so to linearly compress said compressible segment in the vessel;
- wherein said outwardly displaceable portion is configurable between a first condition arranged for delivery through the vasculature and a second condition arranged for abrading at least a portion of the vessel wall, wherein in said second condition said outwardly displaceable portion is outwardly displaced relative to the configuration in said first condition;
- wherein said outwardly displaceable portion is configured to move outwardly toward the interior surface of the vascular vessel and into said second condition when said compressible segment is linearly compressed in the vessel;
- wherein in an outwardly displaced configuration said outwardly displaceable portion has an outer surface having a concave portion and a convex portion;
- wherein said concave portion has a length along said longitudinal axis and said convex portion has a length along said longitudinal axis;
- wherein said length of said concave portion is greater than said length of said convex portion; and
- wherein said linearly compressible segment includes weakened portions including a plurality of joints extending along the longitudinal axis of the intermediate region of the linearly compressible segment.

8. The medical product of claim 7, wherein said actuating member is actuatable to elongate said compressible segment in the vessel.

9. The medical product of claim 7, wherein said one or more abrasive adaptations comprise abrasive particles.

* * * * *